US011505832B2

(12) United States Patent
Gutin et al.

(10) Patent No.: US 11,505,832 B2
(45) Date of Patent: Nov. 22, 2022

(54) METHOD OF USING BIOMARKERS AND CLINICAL VARIABLES FOR PREDICTING CHEMOTHERAPY BENEFIT

(71) Applicant: MYRIAD GENETICS, INC., Salt Lake City, UT (US)

(72) Inventors: Alexander Gutin, Salt Lake City, UT (US); Julia Reid, Salt Lake City, UT (US); Ralf Kronenwett, Salt Lake City, UT (US); Marsel Scheer, Salt Lake City, UT (US)

(73) Assignee: MYRIAD GENETICS, INC., Salt Lake City, UT (US)

( * ) Notice: Subject to any disclaimer, the term of this patent is extended or adjusted under 35 U.S.C. 154(b) by 437 days.

(21) Appl. No.: 16/809,338

(22) Filed: Mar. 4, 2020

(65) Prior Publication Data

US 2020/0283855 A1 Sep. 10, 2020

Related U.S. Application Data

(63) Continuation of application No. PCT/US2018/050014, filed on Sep. 7, 2018.

(60) Provisional application No. 62/555,738, filed on Sep. 8, 2017.

(51) Int. Cl.
*C12Q 1/6886* (2018.01)
*G16H 70/60* (2018.01)
*G16H 50/20* (2018.01)
*G16H 20/10* (2018.01)
*G16B 25/10* (2019.01)
*G16B 20/00* (2019.01)

(52) U.S. Cl.
CPC .......... *C12Q 1/6886* (2013.01); *G16B 20/00* (2019.02); *G16B 25/10* (2019.02); *G16H 20/10* (2018.01); *G16H 50/20* (2018.01); *G16H 70/60* (2018.01); *C12Q 2600/106* (2013.01); *C12Q 2600/118* (2013.01); *C12Q 2600/158* (2013.01)

(58) Field of Classification Search
CPC ....... C12Q 1/6886; G16H 70/60; G16H 60/20
USPC .......................................................... 703/11
See application file for complete search history.

(56) References Cited

U.S. PATENT DOCUMENTS

| | | |
|---|---|---|
| 2006/0024692 A1 | 2/2006 | Nakamura |
| 2006/0166231 A1 | 7/2006 | Baker |
| 2006/0234287 A1 | 10/2006 | Erlander |
| 2007/0099209 A1 | 5/2007 | Clarke |
| 2007/0134688 A1 | 6/2007 | Symmans |
| 2008/0125581 A1 | 5/2008 | Deming |
| 2010/0105564 A1 | 4/2010 | Park |
| 2011/0145176 A1 | 6/2011 | Perou |
| 2011/0306513 A1 | 12/2011 | Song |
| 2012/0065084 A1 | 3/2012 | Sotiriou |
| 2012/0142624 A1 | 6/2012 | Yang |
| 2013/0065786 A1 | 3/2013 | Dartmann |
| 2014/0349878 A1 | 11/2014 | Wang |

FOREIGN PATENT DOCUMENTS

| | | |
|---|---|---|
| CN | 106480201 | 3/2017 |
| EP | 1134738 | 9/2001 |
| EP | 2036988 | 3/2009 |
| EP | 2163649 | 3/2010 |
| EP | 2553118 | 2/2013 |
| EP | 2737081 | 6/2014 |
| WO | 2003001985 | 1/2003 |
| WO | 2006084272 | 8/2006 |
| WO | 2006119593 | 11/2006 |
| WO | 2006119593 A1 | 11/2006 |
| WO | 2006133923 | 12/2006 |
| WO | 2006138275 | 12/2006 |
| WO | 2008006517 | 1/2008 |
| WO | 2008070571 | 6/2008 |
| WO | 2008079269 | 7/2008 |
| WO | 2008154249 | 12/2008 |
| WO | 2009095319 | 8/2009 |
| WO | 2009114836 | 9/2009 |
| WO | 2009132928 | 11/2009 |
| WO | 2009158143 | 12/2009 |
| WO | 2010003771 | 1/2010 |
| WO | 2010003773 | 1/2010 |
| WO | 2010076322 | 7/2010 |
| WO | 2011120984 | 10/2011 |
| WO | 2011121028 | 10/2011 |
| WO | 2012153187 | 11/2012 |
| WO | 2013014296 | 1/2013 |
| WO | 2013188600 | 12/2013 |
| WO | 2015121300 | 8/2015 |

OTHER PUBLICATIONS

"Affymetrix Genechip bHuman Genome U133 plus 2.0 Array", Nov. 7, 2003 (Nov. 7, 2003), GEO.
Akech et al., Biochemical and Biophysical Research Communications, vol. 333, No. 1, 2005, pp. 35-41.
Andre et al., JCO, vol. 26, No. 16, 2008, pp. 2636-2643.
Bayne, Molecular Profiling of the Human Testis Reveals Stringent Pathway-Specific Regulation of RNA Expression Following Gonadotropin Suppression and Progestogen Treatment, Journal of Andrology, 2008, vol. 29, No. 4, pp. 389-403.
Benner et al., Trends in Genetics, vol. 17, 2001, pp. 414-418.
Chanrion et al: A Gene Expression Signature that can Predict the Recurrence of Tamoxifen-Treated Primary Breast Cancer, Clinical Cancer Research, The American Association for Cancer Research, US, vol. 14, No. 6, Mar. 5, 2008 (Mar. 15, 2008), pp. 1744-1752.

(Continued)

*Primary Examiner* — Raymond J Henley, III
(74) *Attorney, Agent, or Firm* — Foley & Lardner LLP

(57) ABSTRACT

Provided herein are methods for predicting chemotherapy benefit. The invention predicts chemotherapy benefit based on the expression analysis of biomarkers, e.g., RNA biomarker transcription analysis, taken from a tumor sample. The biomarker expression data can be combined with clinical variables, e.g., tumor size and nodal status, to generate a profile that predicts the benefit of including chemotherapy as a treatment decision.

20 Claims, 3 Drawing Sheets

(56) References Cited

OTHER PUBLICATIONS

Chanrion, et al., "A gene expression signature that can predict the recurrence of tamoxifen-treated primary breast cancer.", Clinical Cancer Research : An Official Journal of the American Association for Cancer Research Mar. 15, 2008 LNKD—PUBMED:18347175, (Mar. 15, 2008), vol. 14, No. 6, ISSN 1078-0432, pp. 1744-1752.
Cheung et al., Nature Genetics, vol. 33, 2003, pp. 422-425.
Couzin-Frankel et al., Science, vol. 329, 2010, pp. 614-615.
Dai et al., Cancer Research, vol. 65, No. 10, 2005, pp. 4059-4066.
Decock et al., BMC Cancer, vol. 8, No. 1, 2008, pp. 1-8.
Desmedt et al., Cell Cycle, vol. 5, No. 9, 2006, pp. 2198-2202.
Dondoni et al., Angew Cehm Int Ed Engl, 2008, vol. 47, No. 47, pp. 8995-8997.
Dorssers et al., Breast Cancer Research, vol. 7, No. 1, 2004, pp. R82-R92.
Esteva et al., Clin. Cancer Res, vol. 11, 2005, pp. 3315-3319.
Extended European Search Report from Application 14188791 dated Feb. 6, 2015.
Extended European Search Report from Application 16180991.8 dated Jan. 26, 2017.
Extended European Search Report from Application No. 16159481.7, dated Sep. 8, 2016.
Extended European Search Report from Application No. 16184484.0, dated Feb. 9, 2017.
Extended European Search Report from Application No. 18853890.4, dated Apr. 19, 2021.
Filipits et al. Clin Cancer Res. 2011. 17(18):6012-6020. (Year: 2011).
Ganz et al., JNCI, vol. 94, No. 1, 2002, pp. 39-49.
Gao et al., Chinese Medical Journal, vol. 121, No. 16, 2008, pp. 1563-1568.
Gianni et al., JCO, vol. 27, 2009, pp. 2474-2481.
Glas et al., BMC Genomics, vol. 7, No. 278, 2006, pp. 1-10.
Greenbaum et al., Genome Biology, vol. 4, No. 117, 2003, pp. 1-8.
Habel et al., Breast Cancer Research, vol. 8, 2006, pp. 1-15.
Henderson et al., Journal of Clinical Oncology, vol. 21, No. 6, 2003, pp. 976-983.
Hess et al., J Clin Oncol., vol. 24, No. 26, 2006, pp. 4236-4244.
Hess et al., Journal of Clinical Oncology, vol. 29, No. 34, 2011, pp. 4516-4525.
Hou et al., J Neurosci Meth, Oct. 2005, vol. 148, No. 1, pp. 60-70.
International Preliminary Report on Patentability from Application No. PCT/EP2009/057418, dated Dec. 18, 2010.
International Preliminary Report on Patentability from Application No. PCT/EP2009/057426, dated Dec. 18, 2010.
International Preliminary Report on Patentability from Application No. PCT/EP2011/054855, dated Oct. 2, 2012.
International Preliminary Report on Patentability from Application No. PCT/EP2014/051937, dated Aug. 4, 2015.
International Preliminary Report on Patentability from Application No. PCT/EP2015/052081, dated Aug. 18, 2016.
International Preliminary Report on Patentability from Application No. PCT/US2010/024603, dated Sep. 28, 2010.
International Preliminary Report on Patentability from Application PCT/EP2012/064865, dated Jan. 28, 2014.
International Search Report and Written Opinion from Application No. PCT/EP2017/055601, dated Apr. 18, 2017.
International Search Report and Written Opinion issued in PCT/US2018/050014 dated May 17, 2019 (12 pages).
International Search Report from Application No. PCT/EP11/054855, dated Sep. 21, 2011.
International Search Report from Application No. PCT/EP2009/057418, dated Nov. 5, 2009.
International Search Report from Application No. PCT/EP2009/057426, dated Nov. 2, 2009.
International Search Report from Application No. PCT/EP2012/064865 dated Dec. 18, 2012.
International Search Report from Application No. PCT/EP2012/064865, dated Dec. 18, 2012 (6 pages).
International Search Report from Application No. PCT/EP2014/051937, dated Apr. 1, 2014.
International Search Report from Application No. PCT/US2010/024603, dated Sep. 28, 2010.
International Written Opinion from Application No. PCT/EP2012/064865 dated Dec. 18, 2012.
Jemal et al., CA Cancer J Clin, 2011, vol. 61, No. 2, pp. 134.
Liedtke et al., Journal of Clinical Oncology, 2009, vol. 27, No. 19, pp. 3185-3191.
Lin et al., J Neurochem, Jan. 2008, vol. 104, No. 2, pp. 400-408.
Liu et al., PLOS One, vol. 7, No. 5, 2012, pp. e36383.
Loussouarn, et al., "Validation of UBE2C protein as a prognostic marker in node-positive breast cancer.", British Journal of Cancer Jul. 7, 2009 LNKD—PUBMED:19513072, (Jul. 7, 2009), vol. 101, No. 1, ISSN 1532-1827, pp. 166-173.
Lu et al., Clinical Cancer Research, vol. 10, 2004, pp. 3291-3300.
Martin et al., PLOS One, vol. 3, No. 8, 2008, pp. e2994-1-e2994-9.
May et al., Science, vol. 241, 1988, pp. 1441-1449.
Misset et al. Journal of Clinical Oncology, 1996, vol. 14, No. 4, pp. 1136-1145.
Nowak et al, Nature, May 2002, vol. 417, No. 6887, pp. 424-428.
O'Neill et al., Molecular Cancer, 2013, vol. 12, No. 69, pp. 1-9.
Paik, et al., "A Multigene Assay to Predict Recurrence of Tamoxifen-Treated, Node-Negative Breast Cancer", New England Journal of Medicine, Massachusetts Medical Society, Boston, MA, US, (Dec. 30, 2004), vol. 351, No. 27, ISSN 1533-4406, pp. 2817-2826.
Partial European Search Report from Application No. 11175852, dated Nov. 9, 2011.
Pockaj et al., Annals of Surgical Oncology, vol. 11, No. 3, 2004, pp. 328-339.
Rathnagiriswaran et al., Mar. 2010, Int. J. Oncol. vol. 36, No. 3, p. 607-616.
Robbiani et al., "AID Is Required for the Chromosomal Breaks in c-myc that Lead to c-myc/IgH Translocations", Cell, vol. 135, No. 6, pp. 1028-1038.
Ross et al., The Oncologist, vol. 13, No. 5, 2008, pp. 477-493.
Saito-Hisaminato et al., DNA Research, vol. 9, 2002, pp. 35-45.
Shapiro et al., N Engl J Med, vol. 344, 2001, pp. 1997-2008.
Soonmyung et al., "Technology Insight: application of molecular techniques to formalin-fixed parrafin-embedded issues from breast cancer", Natures Clinical Practice Oncology, vol. 2, No. 5, 2005, pp. 246-254.
Sorlie, et al., "Gene expression patterns of breast carcinomas distinguish tumor subclasses with clinical implications", Proceedings of the National Academy of Sciences of the United States (PNAS), National Academy of Science, US, (Sep. 11, 2001), vol. 98, No. 19, ISSN 0027-8424, pp. 10869-10874.
Sotiriou et al. Journal of the National Cancer Institute, 2006, vol. 98, No. 4, pp. 262-272.
Tabchy et al., Clinical Cancer Research, 2010, vol. 16, No. 21, pp. 5351-5361.
Takahashi H., et al., Cancer diagnosis marker extraction for soft tissue sarcomas based on gene expression profiling lata by using projective adaptive resonance theory (PART) filtering method, BMC Bioinformatics, Jul. 2006, 399, pp. 1-11.
Taylor et al., "Dynamic Changes in Gene Expression in Vivo Predict Prognosis of Tamoxifen-Treated Patients With Breast Cancer", Breast Cancer Res., 12 (3), R39 2010.
Taylor Karen J. etal: Dynamic changes in gene expression in vivo predict prognosis of tamoxifen-treated patients with breast cancer, Breast Cancer Research, Current Science, London, GB. vol. 12, No. 3, Jun. 22, 2010 (Jun. 22, 2010), p. R39.
Terasaka S., et al., Using a Customized DNA Microarray for Expression Profiling of the Estrogen-Responsive Genes to Evaluate Estrogen Activity among Natural Estrogens and Industrial Chemicals, Environmental Health Perspectives, 2004, vol. 112, No. 7, pp. 773-781.
Tian et al., Tissue Eng Mar.-Apr. 2005, vol. 11, No. 3-4, pp. 513-525.
Vandesompele et al., Genome Biology, vol. 3, 2002, pp. 1-11.
Veer et al., Nature, vol. 415, 2002, pp. 530-536.

(56) References Cited

OTHER PUBLICATIONS

Vegran et al., British Journal of Cancer, 2009, vol. 101, No. 8, pp. 1357-1364.
Villeneuve et al., Breast Cancer and Treatment, vol. 96, No. 1, 2006, pp. 17-39.
Von Minckwitz, et al., "Validated 3 Gene Signature Predicts Response to Neo-Adjuvant Chemotherapy in Luminal Breast Cancer—Results from GeparTrio and GeparQuattro", Cancer Research, American Association for Cancer Rerearch, US, (Dec. 1, 2009), vol. 69, No. 24, suppl, ISSN 0008-5472, p. 635S.
Wang et al., Cancer Letters, vol. 272, No. 2, 2008, pp. 277-284.
Wang et al., Lancet, vol. 365, No. 9460, 2005, pp. 671-679.
Warf et al., "Analytcal validation of a 12-gene molecular test for the prediction of distant recurrence in breast cancer", Future Sci OA. Jun. 5, 2017;3(3):FSO221. doi: 10.4155/fsoa-2017-0051. eCollection Aug. 2017.
Wray et al., vol. 121, No. 21, Apr. 8, 2013, pp. 4359-4365.
Written Opinion issued in Application No. PCT/EP2011/054855, dated Jun. 24, 2016 (25 pages).
Yu, et al., "Pathway analysis of gene signatures predicting metastasis of node-negative primary breast cancer.", BMC Cancer (Sep. 25, 2007), vol. 7, No. 182, Article No. 182.
Zhijuan et al., Oncology Reports, vol. 20, 2008, pp. 325-332.

METHOD OF USING BIOMARKERS AND CLINICAL VARIABLES FOR PREDICTING CHEMOTHERAPY BENEFIT

This application is a continuation of International Patent Application No. PCT/US2018/050014, filed Sep. 7, 2018, which claims priority benefit to U.S. Provisional Application No. 62/555,738, filed Sep. 8, 2017, the entire contents of each of which are hereby incorporated by reference.

BACKGROUND

Breast cancer is the most common tumor type and one of the leading causes of cancer-related death in women (Jemal et al., *CA Cancer J Clin.*, 2011). It is estimated that every tenth woman will develop breast cancer during her lifetime. Although the incidence has increased over the years, the mortality has constantly decreased due to the advances in early detection and the development of novel effective treatment strategies.

Breast cancer patients are frequently treated with radiotherapy, hormone therapy or cytotoxic chemotherapy after surgery (adjuvant treatment) to control for residual tumor cells and reduce the risk of recurrence. Chemotherapy includes the combined use of several cytotoxic agents, whereas anthracycline and taxane-based treatment strategies have been shown to be superior compared to other standard combination therapies (Misset et al., *J Clin Oncol.*, 1996, Henderson et al., *J Clin Oncol.*, 2003).

Systemic chemotherapy is commonly applied to reduce the likelihood of recurrence in HER2/neu-positive and in tumors lacking expression of the estrogen receptor and HER2/neu receptor (triple negative, basal). The most challenging treatment decision concerns luminal (estrogen receptor positive and HER2/neu-negative) tumors for which classical clinical factors like grading, tumor size or lymph node involvement do not provide a clear answer to the question whether to use chemotherapy or not.

Chemotherapy can also be applied in the neoadjuvant (preoperative) setting in which breast cancer patients receive systemic therapy before the remaining tumor cells are removed by surgery. Neoadjuvant chemotherapy of early breast cancer leads to high clinical response rates of 70-90%. However, in the majority of clinical responders, the pathological assessment of the tumor residue reveals the presence of residual tumor cell foci. A complete eradication of cancer cells in the breast and lymph nodes after neoadjuvant treatment is called pathological complete response (pCR) and observed in only 10-25% of all patients. The pCR is an appropriate surrogate marker for disease-free survival and a strong indicator of benefit from chemotherapy.

The preoperative treatment strategy provides the opportunity to directly assess the response of a particular tumor to the applied therapy: the reduction of the tumor mass in response to therapy can be directly monitored. For patients with a low probability of response, other therapeutic approaches should be considered. Biomarkers can be analyzed from pretherapeutic core biopsies to identify the most valuable predictive markers. A common approach is to isolate RNA from core biopsies for the gene expression analysis before neoadjuvant therapy. Afterwards the therapeutic success can be directly evaluated by the tumor reduction and correlated with the gene expression data.

Predictive multigene assays like the DLDA30 (Hess et al., *J Clin Oncol.*, 2006) have been shown to provide information beyond clinical parameters like tumor grading and hormone receptor status in breast cancer patients treated with neoadjuvant therapy. However, the predictive multigene test DLDA30 was established without considering the estrogen receptor status. Therefore the test might reflect phenotypic differences between complete responder and nonresponder, responders being predominantly ER-negative and HER2/neu positive (Tabchy et al., Clin Can Res, 2010).

Additionally, established multigene tests for prognosis were analyzed in the neoadjuvant setting to assess whether the prognostic assays can also predict chemosensitivity. One example is the Genomic Grade Index (GGI), a multigene test to define histologic grade based on gene expression profiles (Sotiriou et al, JNCI, 2006). It was demonstrated by Liedtke and colleagues that a high GGI is associated with increased chemosensitivity in breast cancer patients treated with neoadjuvant therapy (Liedtke, *J Clin Oncol,* 2009).

The EndoPredict® score (EP score) is a multivariate score for determining the risk of remote metastases in patients with an estrogen receptor-positive and HER2-negative primary mammary carcinoma under a sole adjuvant endocrine therapy (Filipits et al. Clin. Cancer Res. 17:6012-20 (2011): A new molecular predictor of distant recurrence in ER-positive, HER2-negative breast cancer adds independent information to conventional clinical risk factors; EP 2 553 118 B1; PCT/EP2017/055601)). The EP score is a numerical measure of the relative risk that the tumor of the breast cancer patient examined with this EP score will develop remote metastases within 10 years. The determined risk thus can be used to support the decision whether breast cancer patients should be treated with chemotherapy, or whether a milder hormone therapy is sufficient as a treatment. Patients with a relative risk of metastases under an endocrine therapy of more than 10% usually undergo chemotherapy. If the risk of metastases is lower, most physicians recommend the milder hormone therapy.

Although gene signatures have been shown to predict chemotherapy response, large-scale validation studies including clinical follow-up data that analyze factors such as tumor size and nodal status are incomplete and not commonly used to guide treatment decisions in a clinical setting. To reduce the number of patients suffering from serious side effects without a clear benefit of systemic therapy, there is a great need for molecular biomarkers in combination with clinical factors, such as tumor size and nodal status, to predict the sensitivity to chemotherapy and thus allow a more tailored treatment strategy. The present invention fulfills the need for advanced methods for predicting chemotherapy benefit.

SUMMARY

In an embodiment, a method for predicting a response to and/or a benefit of chemotherapy is provided. The method comprises including neoadjuvant chemotherapy, in a patient suffering from or at risk of developing recurrent neoplastic disease, in particular breast cancer, said method comprising the steps of: (a) determining RNA expression level values of four or more of the following 8 genes in a tumor sample from the patient: UBE2C, BIRC5, DHCR7, STC2, AZGP1, RBBP8, IL6ST and MGP; or determining the RNA expression levels of four or more of the following 8 genes in a tumor sample from the patient: UBE2C, RACGAP1, DHCR7, STC2, AZGP1, RBBP8, IL6ST and MGP; (b) generating an expression score by combining the expression level values for the genes of the mentioned set recited in (a); (c) generating a clinical values score; and (d) mathematically combining the expression score with the clinical values score to generate a combined score wherein the combined score is indicative of a prognosis for the patient. In an embodiment, the prognosis is correlated to one or more distant metastases. In an embodiment, the prognosis predicts a response to chemotherapy. In an embodiment, the chemotherapy is adjuvant chemotherapy. In an embodiment the chemotherapy includes an anthracyclin-based therapy. In an embodiment, the chemotherapy is 5-fluorouracil, epirubicin, and cyclophosphamide (FEC). In an embodiment, the RNA expression levels have at least in part not been normalized before the mathematical combination. In an embodiment, the clinical values score is generating by processing information regarding nodal status of the patient. In an embodiment, the clinical values score is generating by processing information regarding tumor size. In an embodiment, the clinical values score is generated by processing information regarding tumor size and nodal status. In an embodiment, said expression level is determined by at least one of a PCR based method, a micorarray based method, or a hybridization based method, a sequencing and/or next generation sequencing approach. In an embodiment, said determination of expression levels is in a formalin-fixed paraffin-embedded tumor sample or in a fresh-frozen tumor sample. In an embodiment, the expression level of said at least one marker gene is determined as a pattern of expression relative to at least one reference gene or to a computed average expression value. In an embodiment, said step of mathematically combining comprises a step of applying an algorithm to values representative of an expression level of a given gene, in particular wherein said algorithm is a linear combination of said values representative of an expression level of a given gene, or wherein a value for a representative of an expression level of a given gene is multiplied with a coefficient. In an embodiment, one, two or more thresholds are determined for said combined score and discriminated into high and low risk, high, intermediate and low risk, or more risk groups by applying the threshold on the combined score. In an embodiment, a high combined score is indicative of benefit from a more aggressive therapy. In an embodiment, the patient is node positive. In an embodiment, the four or more genes comprises UBE2C, BIRC5, DHCR7, STC2, AZGP1, RBBP8, IL6ST and MGP. In an embodiment, the four or more genes comprises UBE2C, RACGAP1, DHCR7, STC2, AZGP1, RBBP8, IL6ST and MGP. In an embodiment, the neoplastic disease is an estrogen receptor-positive and HER2-negative breast cancer.

In another embodiment, a computer program product stored on a data carrier or implemented on a diagnostic system is provided. The computer program is capable of outputting values representative of an expression level of a given gene, such as a real time PCR system capable of processing values representative of an expression level values of a combination of genes and clinical variables, and mathematically combining said values to yield a combined score, wherein said combined score is predicting said response and/or a benefit of chemotherapy.

DETAILED DESCRIPTION

Figure 1:
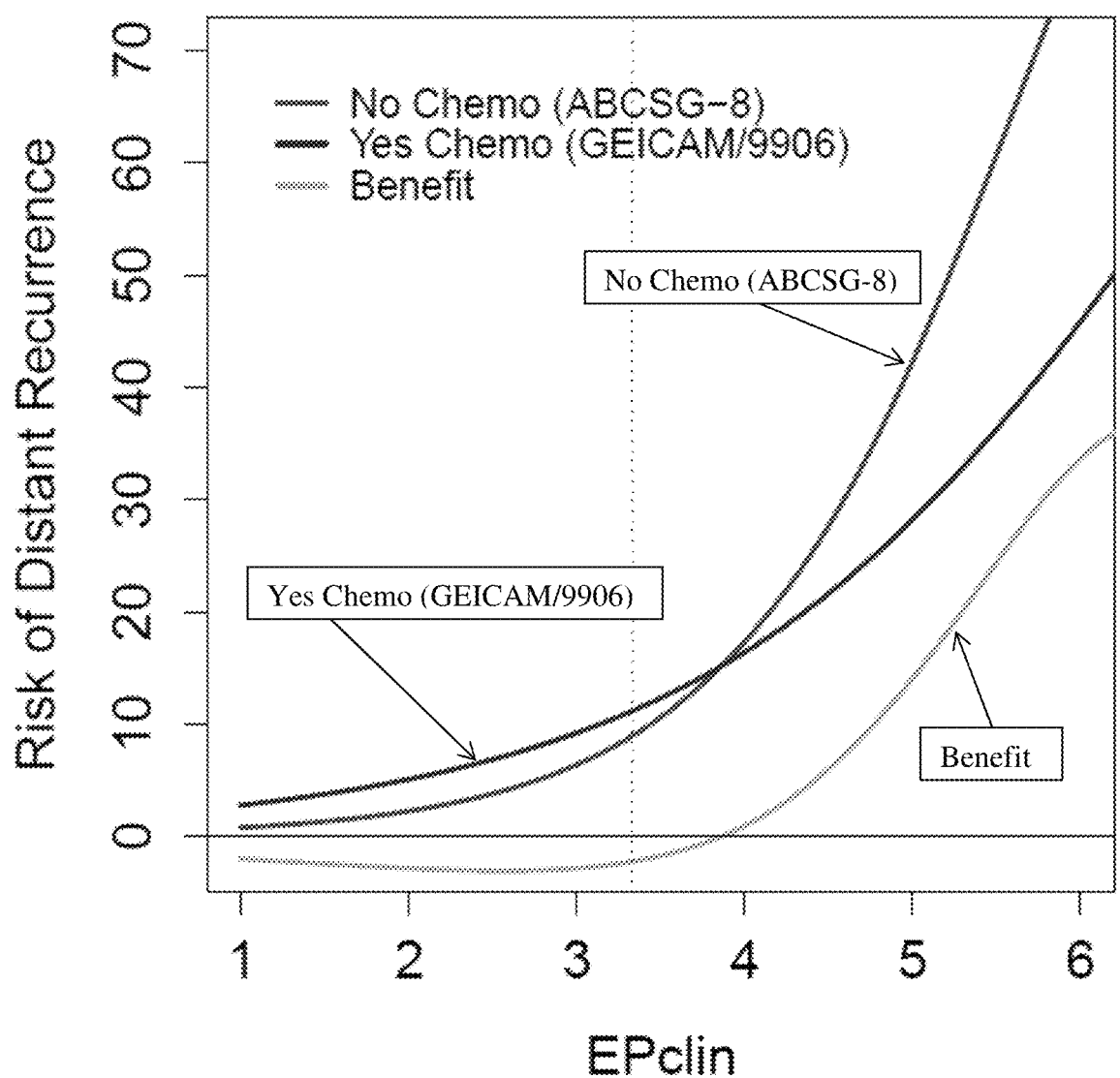
FIG. 1 demonstrates the use of EPclin to predict the benefit of chemotherapy in node positive and node negative samples.

The present invention provides methods of predicting chemotherapy benefit based on the expression analysis of biomarkers taken from a tumor sample in combination with clinical variables including tumor size and nodal status.

Definitions

Unless defined otherwise, technical and scientific terms used herein have the same meaning as commonly understood by one of ordinary skill in the art to which this invention belongs.

The term "cancer" refer to or describe the physiological condition in mammals that is typically characterized by unregulated cell growth. The term "cancer" as used herein includes carcinomas, (e.g., carcinoma in situ, invasive carcinoma, metastatic carcinoma) and pre-malignant conditions, neomorphic changes independent of their histological origin. The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer and primary carcinomas are included.

The term "tumor" as used herein, refers to all neoplastic cell growth and proliferation, whether malignant or benign, and all pre-cancerous and cancerous cells and tissues.

The term "prediction", as used herein, relates to an individual assessment of the malignancy of a tumor, or to the expected survival rate (OAS, overall survival or DFS, disease free survival) of a patient, if the tumor is treated with a given therapy. In contrast thereto, the term "prognosis" relates to an individual assessment of the malignancy of a tumor, or to the expected survival rate (OAS, overall survival or DFS, disease free survival) of a patient, if the tumor remains untreated.

The term "Predicting the response to chemotherapy", within the meaning of the invention, shall be understood to be the act of determining a likely outcome of cytotoxic chemotherapy in a patient affected by cancer. The prediction of a response is preferably made with reference to probability values for reaching a desired or non-desired outcome of the chemotherapy. The predictive methods of the present invention can be used clinically to make treatment decisions by choosing the most appropriate treatment modalities for any particular patient.

The phrase "predicting an outcome" of a disease, as used herein, is meant to include both a prediction of an outcome of a patient undergoing a given therapy and a prognosis of a patient who is not treated. The term "predicting an outcome" may, in particular, relate to the risk of a patient developing metastasis, local recurrence or death.

The phrase "response of a tumor to chemotherapy", within the meaning of the invention, relates to any response of the tumor to cytotoxic chemotherapy, preferably to a change in tumor mass and/or volume after initiation of neoadjuvant chemotherapy and/or prolongation of time to distant metastasis or time to death following neoadjuvant or adjuvant chemotherapy. Tumor response may be assessed in a neoadjuvant situation where the size of a tumor after systemic intervention can be compared to the initial size and dimensions as measured by CT, PET, mammo-gram, ultrasound or palpation, usually recorded as "clinical response" of a patient. Response may also be assessed by caliper measurement or pathological examination of the tumor after biopsy or surgical resection. Response may be recorded in a quantitative fashion like percentage change in tumor volume or in a qualitative fashion like "no change" (NC), "partial remission" (PR), "complete remission" (CR) or other qualitative criteria. Assessment of tumor response may be done early after the onset of neoadjuvant therapy e.g., after a few hours, days, weeks or preferably after a few months. A typical endpoint for response assessment is upon termination of neoadjuvant chemotherapy or upon surgical removal of residual tumor cells and/or the tumor bed. This is typically three month after initiation of neoadjuvanttherapy. Response may also be assessed by comparing time to distant metastasis or death of a patient following neoadjuvant or adjuvant chemotherapy with time to distant metastasis or death of a patient not treated with chemotherapy.

The term "pathological complete response" (pCR), as used herein, relates to a complete disappearance or absence of invasive tumor cells in the breast and/or lymph nodes as assessed by a histopathological examination of the surgical specimen following neoadjuvant chemotherapy.

An "outcome" within the meaning of the present invention is a defined condition attained in the course of the disease. This disease outcome may e.g. be a clinical condition such as "recurrence of disease", "development of metastasis", "development of nodal metastasis", development of distant metastasis", "survival", "death", "tumor remission rate", a disease stage or grade or the like.

A "risk" is understood to be a number related to the probability of a subject or a patient to develop or arrive at a certain disease outcome. The term "risk" in the context of the present invention is not meant to carry any positive or negative connotation with regard to a patient's wellbeing but merely refers to a probability or likelihood of an occurrence or development of a given condition.

The term "prognosis" as used herein, relates to an individual assessment of the malignancy of a tumor, or to the expected response if there is no drug therapy. In contrast thereto, the term "prediction" relates to an individual assessment of the malignancy of a tumor, or to the expected response if the therapy contains a drug in comparison to the malignancy or response without this drug.

The term "clinical data" relates to the entirety of available data and information concerning the health status of a patient including, but not limited to, tumor stage, tumor size, tumor metastasis status, nodal status, age, sex, weight, menopausal/hormonal status, etiopathology data, anamnesis data, data obtained by in vitro diagnostic methods such as histopathology, blood or urine tests, data obtained by imaging methods, such as x-ray, computed tomography, MRI, PET, spect, ultrasound, electrophysiological data, genetic analysis, gene expression analysis, biopsy evaluation, intraoperative findings.

The term "node positive", "diagnosed as node positive", "node involvement" or "lymph node involvement" means a patient having previously been diagnosed with lymph node metastasis. It shall encompass both draining lymph node, near lymph node, and distant lymph node metastasis. This previous diagnosis itself shall not form part of the inventive method. Rather it is a precondition for selecting patients whose samples may be used for one embodiment of the present invention. This previous diagnosis may have been arrived at by any suitable method known in the art, including, but not limited to lymph node removal and pathological analysis, biopsy analysis, in-vitro analysis of biomarkers indicative for metastasis, imaging methods (e.g. computed tomography, X-ray, magnetic resonance imaging, ultrasound), and intraoperative findings.

The term "sample", as used herein, refers to a sample obtained from a patient. The sample may be of any biological tissue or fluid. Such samples include, but are not limited to, sputum, blood, serum, plasma, blood cells (e.g., white cells), tissue, core or fine needle biopsy samples, cell-containing body fluids, free floating nucleic acids, urine, peritoneal fluid, and pleural fluid, or cells there from. Biological samples may also include sections of tissues such as frozen or fixed sections taken for histological purposes or microdissected cells or extracellular parts thereof. A biological sample to be analyzed is tissue material from neoplastic lesion taken by aspiration or punctuation, excision or by any other surgical method leading to biopsy or resected cellular material. Such biological sample may comprise cells obtained from a patient. The cells may be found in a cell "smear" collected, for example, by a nipple aspiration, ductal lavage, fine needle biopsy or from provoked or spontaneous nipple discharge. In another embodiment, the sample is a body fluid. Such fluids include, for example, blood fluids, serum, plasma, lymph, ascitic fluids, gynecological fluids, or urine but not limited to these fluids.

A "tumor sample" is a biological sample containing tumor cells, whether intact or degraded. The sample may be of any biological tissue or fluid. Such samples include, but are not limited to, sputum, blood, serum, plasma, blood cells (e.g., white cells), tissue, core or fine needle biopsy samples, cell-containing body fluids, urine, peritoneal fluid, and pleural fluid, liquor cerebrospinalis, tear fluid, or cells isolated therefrom. This may also include sections of tissues such as frozen or fixed sections taken for histological purposes or microdissected cells or extracellular parts thereof. A tumor sample to be analyzed can be tissue material from a neoplastic lesion taken by aspiration or punctuation, excision or by any other surgical method leading to biopsy or resected cellular material. Such comprises tumor cells or tumor cell fragments obtained from the patient. The cells may be found in a cell "smear" collected, for example, by a nipple aspiration, ductal lavage, fine needle biopsy or from provoked or spontaneous nipple discharge. In another embodiment, the sample is a body fluid. Such fluids include, for example, blood fluids, serum, plasma, lymph, ascitic fluids, gynecologic fluids, or urine but not limited to these fluids.

A "gene" is a set of segments of nucleic acid that contains the information necessary to produce a functional RNA product. A "gene product" is a biological molecule produced through transcription or expression of a gene, e.g., an mRNA, cDNA or the translated protein.

An "mRNA" is the transcribed product of a gene and shall have the ordinary meaning understood by a person skilled in the art. A "molecule derived from an mRNA" is a molecule which is chemically or enzymatically obtained from an mRNA template, such as cDNA.

The term "marker" or "biomarker" refers to a biological molecule, e.g., a nucleic acid, peptide, protein, hormone, etc., whose presence or concentration can be detected and correlated with a known condition, such as a disease state. The term "predictive marker" relates to a marker which can be used to predict the clinical response of a patient towards a given treatment.

The term "expression level" refers to a determined level of gene expression. This may be a determined level of gene expression as an absolute value or compared to a reference gene (e.g. a housekeeping gene), to the average of two or more reference genes, or to a computed average expression value (e.g. in DNA chip analysis) or to another informative gene without the use of a reference sample. The expression level of a gene may be measured directly, e.g. by obtaining a signal wherein the signal strength is correlated to the amount of mRNA transcripts of that gene or it may be obtained indirectly at a protein level, e.g., by immunohistochemistry, CISH, ELISA or RIA methods. The expression level may also be obtained by way of a competitive reaction to a reference sample. An expression value which is determined by measuring some physical parameter in an assay, e.g. fluorescence emission, may be assigned a numerical value which may be used for further processing of information.

A "reference pattern of expression levels" within the meaning of the invention shall be understood as being any pattern of expression levels that can be used for the comparison to another pattern of expression levels. In a preferred embodiment of the invention, a reference pattern of expression levels is, e.g., an average pattern of expression levels observed in a group of healthy individuals, diseased individuals, or diseased individuals having received a particular type of therapy, serving as a reference group, or individuals with good or bad outcome.

The term "mathematically combining expression levels", within the meaning of the invention shall be understood as deriving a numeric value from a determined expression level of a gene and applying an algorithm to one or more of such numeric values to obtain a combined numerical value or combined score.

An "algorithm" is a process that performs some sequence of operations to produce information.

The term "score" within the meaning of the invention shall be understood as a numeric value, which is related to the outcome of a patient's disease and/or the response of a tumor to chemotherapy. The numeric value is derived by combining the expression levels of marker genes using pre-specified coefficients in a mathematic algorithm. The expression levels can be employed as CT or delta-CT values obtained by kinetic RT-PCR, as absolute or relative fluorescence intensity values obtained through microarrays or by any other method useful to quantify absolute or relative RNA levels. Combining these expression levels can be accomplished for example by multiplying each expression level with a defined and specified coefficient and summing up such products to yield a score. The score may be also derived from expression levels together with other information, e. g. clinical data like tumor size, lymph node status or tumor grading as such variables can also be coded as numbers in an equation. The score may be used on a continuous scale to predict the response of a tumor to chemotherapy and/or the outcome of a patient's disease. Cut-off values may be applied to distinguish clinical relevant subgroups. Cut-off values for such scores can be determined in the same way as cut-off values for conventional diagnostic markers and are well known to those skilled in the art. A useful way of determining such cut-off value is to construct a receiver-operator curve (ROC curve) on the basis of all conceivable cut-off values, determine the single point on the ROC curve with the closest proximity to the upper left corner (0/1) in the ROC plot. Most of the time cut-off values will be determined by less formalized procedures by choosing the combination of sensitivity and specificity determined by such cut-off value providing the most beneficial medical information to the problem investigated.

A "discriminant function" is a function of a set of variables used to classify an object or event. A discriminant function thus allows classification of a patient, sample or event into a category or a plurality of categories according to data or parameters available from said patient, sample or event. Such classification is a standard instrument of statistical analysis well known to the skilled person. For example, a patient may be classified as "high risk" or "low risk", "high probability of metastasis" or "low probability of metastasis," "in need of treatment" or "not in need of treatment" according to data obtained from said patient, sample or event. Classification is not limited to "high vs. low," but may be performed into a plurality of categories, grading or the like. Classification shall also be understood in a wider sense as a discriminating score, where e.g. a higher score represents a higher likelihood of distant metastasis, e.g., the (overall) risk of a distant metastasis. Examples for discriminant functions which allow a classification include, but are not limited to functions defined by support vector machines (SVM), k-nearest neighbors (kNN), (naive) Bayes models, linear regression models or piecewise defined functions such as, for example, in subgroup discovery, in decision trees, in logical analysis of data (LAD) and the like. In a wider sense, continuous score values of mathematical methods or algorithms, such as correlation coefficients, projections, support vector machine scores, other similarity-based methods, combinations of these and the like are examples for illustrative purpose.

The term "therapy" refers to a timely sequential or simultaneous administration of anti-tumor, and/or anti vascular, and/or anti stroma, and/or immune stimulating or suppressive, and/or blood cell proliferative agents, and/or radiation therapy, and/or hyperthermia, and/or hypothermia for cancer therapy. The administration of these can be performed in an adjuvant and/or neoadjuvant mode. The composition of such "protocol" may vary in the dose of each of the single agents, timeframe of application and frequency of administration within a defined therapy window. Currently various combinations of various drugs and/or physical methods, and various schedules are under investigation. A "taxane/anthracycline-containing chemotherapy" is a therapy modality comprising the administration of taxane and/or anthracycline and therapeutically effective derivates thereof. A chemotherapy regimen can also include, for example, 5-fluorouracil, epirubicin, and cyclophosphamide (FEC) and/or FEC followed by weekly paclitaxel (FEX-P).

The term "therapy modality", "therapy mode", "regimen" as well as "therapy regimen" refers to a timely sequential or simultaneous administration of anti-tumor, and/or anti vascular, and/or immune stimulating, and/or blood cell proliferative agents, and/or radiation therapy, and/or hyperthermia, and/or hypothermia for cancer therapy. The administration of these can be performed in an adjuvant and/or neoadjuvant mode. The composition of such "protocol" may vary in the dose of the single agent, timeframe of application and frequency of administration within a defined therapy window. Currently various combinations of various drugs and/or physical methods, and various schedules are under investigation.

The term "cytotoxic chemotherapy" refers to various treatment modalities affecting cell proliferation and/or survival. The treatment may include administration of alkylating agents, antimetabolites, anthracyclines, plant alkaloids, topoisomerase inhibitors, and other antitumor agents, including monoclonal antibodies and kinase inhibitors. In particular, the cytotoxic treatment may relate to a taxane treatment. Taxanes are plant alkaloids which block cell division by preventing microtubule function. The prototype taxane is the natural product paclitaxel, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

The term "neoadjuvant chemotherapy" relates to a preoperative therapy regimen consisting of a panel of hormonal, chemotherapeutic and/or antibody agents, which is aimed to shrink the primary tumor, thereby rendering local therapy (surgery or radiotherapy) less destructive or more effective, enabling breast conserving surgery and evaluation of responsiveness of tumor sensitivity towards specific agents in vivo.

The term "lymph node involvement" means a patient having previously been diagnosed with lymph node metastasis. It shall encompass both draining lymph node, near lymph node, and distant lymph node metastasis. This previous diagnosis itself shall not form part of the inventive method. Rather it is a precondition for selecting patients whose samples may be used for one embodiment of the present invention. This previous diagnosis may have been arrived at by any suitable method known in the art, including, but not limited to lymph node removal and pathological analysis, biopsy analysis, in-vitro analysis of biomarkers indicative for metastasis, imaging methods (e.g., computed tomography, X-ray, magnetic resonance imaging, ultrasound), and intraoperative findings.

The term "endocrine treatment" or "hormonal treatment" (sometimes also referred to as "anti-hormonal treatment") denotes a treatment which targets hormone signaling, e.g. hormone inhibition, hormone receptor inhibition, use of hormone receptor agonists or antagonists, use of scavenger- or orphan receptors, use of hormone derivatives and interference with hormone production. Particular examples are tamoxifene therapy which modulates signaling of the estrogen receptor, or aromatase treatment which interferes with steroid hormone production.

Tamoxifen is an orally active selective estrogen receptor modulator (SERM) that is used in the treatment of breast cancer and is currently the world's largest selling drug for that purpose. Tamoxifen is sold under the trade names Nolvadex, Istubal, and Valodex. However, the drug, even before its patent expiration, was and still is widely referred to by its generic name "tamoxifen." Tamoxifen and Tamoxifen derivatives competitively bind to estrogen receptors on tumors and other tissue targets, producing a nuclear complex that decreases RNA synthesis and inhibits estrogen effects.

Steroid receptors are intracellular receptors (typically cytoplasmic) that perform signal transduction for steroid hormones. Examples include type I Receptors, in particular sex hormone receptors, e.g. androgen receptor, estrogen receptor, progesterone receptor; Glucocorticoid receptor, mineralocorticoid receptor; and type II Receptors, e.g. vitamin A receptor, vitamin D receptor, retinoid receptor, thyroid hormone receptor.

The term "hybridization-based method", as used herein, refers to methods imparting a process of combining complementary, single-stranded nucleic acids or nucleotide analogues into a single double stranded molecule. Nucleotides or nucleotide analogues will bind to their complement under normal conditions, so two perfectly complementary strands will bind to each other readily. In bioanalytics, very often labeled, single stranded probes are used in order to find complementary target sequences. If such sequences exist in the sample, the probes will hybridize to said sequences which can then be detected due to the label. Other hybridization based methods comprise microarray and/or biochip methods. Therein, probes are immobilized on a solid phase, which is then exposed to a sample. If complementary nucleic acids exist in the sample, these will hybridize to the probes and can thus be detected. These approaches are also known as "array based methods." Yet another hybridization based method is PCR, which is described below. When it comes to the determination of expression levels, hybridization based methods may for example be used to determine the amount of mRNA for a given gene.

An oligonucleotide capable of specifically binding sequences a gene or fragments thereof relates to an oligonucleotide which specifically hybridizes to a gene or gene product, such as the gene's mRNA or cDNA or to a fragment thereof. To specifically detect the gene or gene product, it is not necessary to detect the entire gene sequence. A fragment of about 20-150 bases will contain enough sequence specific information to allow specific hybridization.

The term "a PCR based method" as used herein refers to methods comprising a polymerase chain reaction (PCR). This is a method of exponentially amplifying nucleic acids, e.g. DNA by enzymatic replication in vitro. As PCR is an in vitro technique, it can be performed without restrictions on the form of DNA, and it can be extensively modified to perform a wide array of genetic manipulations. When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR). Moreover, PCR-based methods comprise e.g. real time PCR, and, particularly suited for the analysis of expression levels, kinetic or quantitative PCR (qPCR).

The term "Quantitative PCR" (qPCR)" refers to any type of a PCR method which allows the quantification of the template in a sample. Quantitative real-time PCR comprise different techniques of performance or product detection as for example the TaqMan technique or the LightCycler technique. The TaqMan technique, for examples, uses a dual-labelled fluorogenic probe. The TaqMan real-time PCR measures accumulation of a product via the fluorophore during the exponential stages of the PCR, rather than at the end point as in conventional PCR. The exponential increase of the product is used to determine the threshold cycle, CT, e.g., the number of PCR cycles at which a significant exponential increase in fluorescence is detected, and which is directly correlated with the number of copies of DNA template present in the reaction. The setup of the reaction is very similar to a conventional PCR, but is carried out in a real-time thermal cycler that allows measurement of fluorescent molecules in the PCR tubes. Different from regular PCR, in TaqMan real-time PCR a probe is added to the reaction, e.g., a single-stranded oligonucleotide complementary to a segment of 20-60 nucleotides within the DNA template and located between the two primers. A fluorescent reporter or fluorophore (e.g., 6-carboxyfluorescein, acronym: FAM, or tetrachlorofluorescin, acronym: TET) and quencher (e.g., tetramethylrhodamine, acronym: TAMRA, of dihydrocyclopyrroloindole tripeptide 'black hole quencher', acronym: BHQ) are covalently attached to the 5' and 3' ends of the probe, respectively. The close proximity between fluorophore and quencher attached to the probe inhibits fluorescence from the fluorophore. During PCR, as DNA synthesis commences, the 5' to 3' exonuclease activity of the Taq polymerase degrades that proportion of the probe that has annealed to the template. Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

By "array" or "matrix" an arrangement of addressable locations or "addresses" on a device is meant. The locations can be arranged in two dimensional arrays, three dimensional arrays, or other matrix formats. The number of locations can range from several to at least hundreds of thousands. Most importantly, each location represents a totally independent reaction site. Arrays include but are not limited to nucleic acid arrays, protein arrays and antibody arrays. A "nucleic acid array" refers to an array containing nucleic acid probes, such as oligonucleotides, nucleotide analogues, polynucleotides, polymers of nucleotide analogues, morpholinos or larger portions of genes. The nucleic acid and/or analogue on the array is preferably single stranded. Arrays wherein the probes are oligonucleotides are referred to as "oligonucleotide arrays" or "oligonucleotide chips." A "microarray," herein also refers to a "biochip" or "biological chip", an array of regions having a density of discrete regions of at least about 100/cm2, and preferably at least about 1000/cm2.

"Primer pairs" and "probes" within the meaning of the invention shall have the ordinary meaning of this term which is well known to the person skilled in the art of molecular biology. In a preferred embodiment of the invention "primer pairs" and "probes" shall be understood as being polynucleotide molecules having a sequence identical, complementary, homologous, or homologous to the complement of regions of a target polynucleotide which is to be detected or quantified. In yet another embodiment, nucleotide analogues are also comprised for usage as primers and/or probes. Probe technologies used for kinetic or real time PCR applications could be e.g. TaqMan® systems obtainable at Applied Biosystems, extension probes such as Scorpion® Primers, Dual Hybridisation Probes, Amplifluor® obtainable at Chemicon International, Inc, or Minor Groove Binders.

"Individually labeled probes", within the meaning of the invention, shall be understood as being molecular probes comprising a polynucleotide, oligonucleotide or nucleotide analogue and a label, helpful in the detection or quantification of the probe. Preferred labels are fluorescent molecules, luminescent molecules, radioactive molecules, enzymatic molecules and/or quenching molecules.

"Arrayed probes", within the meaning of the invention, shall be understood as being a collection of immobilized probes, preferably in an orderly arrangement. In a preferred embodiment of the invention, the individual "arrayed probes" can be identified by their respective position on the solid support, e.g., on a "chip."

When used in reference to a single-stranded nucleic acid sequence, the term "substantially homologous" refers to any probe that can hybridize (i.e., it is the complement of) the single-stranded nucleic acid sequence under conditions of low stringency as described above.

Use of the Present Teachings for Predicting Chemotherapy Benefit

The EndoPredict® score, derivation of the EndoPredict® biomarkers, algorithms, and necessary technical method for determining it is described in Filipits et al. (2011), and in EP 2553118, and in PCT/EP2017/055601, all of which are incorporated herein by reference in its entirety. Described herein is EPclin, which is the use of EndoPredict in combination with clinical variables, including but not limited to tumor size and nodal status, to predict the benefit of chemotherapy.

An embodiment of the present invention determines whether the marker genes described herein is indicative of a good outcome or a bad outcome in a patient receiving chemotherapy. An embodiment of the present invention combines marker data with clinical variables such as tumor size and nodal status to predict chemotherapy benefit. The skilled person can thus construct a mathematical combination e.g., an algorithm taking into account the effect of a given genes. For example a summation or weighted summation of genes whose overexpression is indicative of a good outcome results in an algorithm wherein a high risk score is indicative of a good outcome. The validity of the algorithm may be examined by analyzing tumor samples of patients with a clinical record, wherein e.g., the score for good outcome patients and bad outcome patients may be determined separately and compared. The skilled person, a biostatistician, will know to apply further mathematical methods, such as discriminate functions to obtain optimized algorithms. Algorithms may be optimized e.g., for sensitivity or specificity. Algorithms may be adapted to the particular analytical platform used to measure gene expression of marker genes, such as quantitative PCR. In an embodiment hazard modeling, for example, Cox modeling, can be used to generate a risk scoring algorithm with outcomes that may include a variety of outcomes, for example, survival or distant metastases.

A high score value indicates an increased likelihood of a pathological complete response after neoadjuvant chemotherapy treatment, a low score value indicates a decreased likelihood of developing a pathological complete response after neoadjuvant treatment. Consequently, a high score also indicates that the patient is a high risk patient who will benefit from a more aggressive therapy, e.g., cytotoxic chemotherapy.

According to an aspect of the invention there is provided a method as described above, wherein a risk of developing recurrence is predicted. According to an aspect of the invention there is provided a method as described above, wherein said expression level is determined as a non-protein expression level. According to an aspect of the invention there is provided a method as described above, wherein said expression level is determined as an RNA expression level. According to an aspect of the invention there is provided a method as described above, wherein said expression level is determined by at least one of a PCR based method, a microarray based method, and a hybridization based method. According to an aspect of the invention there is provided a method as described above, wherein said determination of expression levels is in a formalin-fixed paraffin embedded tumor sample or in a fresh-frozen tumor sample. According to an aspect of the invention there is provided a method as described above, wherein the expression level of said at least on marker gene is determined as a pattern of expression relative to at least one reference gene or to a computed average expression value. According to an aspect of the invention there is provided a method as described above, wherein said step of mathematically combining comprises a step of applying an algorithm to values representative of an expression level of a given gene. According to an aspect of the invention there is provided a method as described above, wherein said algorithm is a linear combination of said values representative of an expression level of a given gene. According to an aspect of the invention there is provided a method as described above, wherein a value for a representative of an expression level of a given gene is multiplied with a coefficient. According to an aspect of the invention there is provided a method as described above, wherein one, two or more thresholds are determined for said combined score and discriminated into high and low risk, high, intermediate and low risk, or more risk groups by applying the threshold on the combined score. According to an aspect of the invention there is provided a method that describes wherein the risk of no chemotherapy is determined. According to an aspect of the invention there is provided a method that describes the absolute and relative benefit of chemotherapy in each risk group.

According to an aspect of the invention there is provided a method as described above, wherein a high combined score is indicative of benefit from a more aggressive therapy, e.g., cytotoxic chemotherapy. The skilled person understands that a "high score" in this regard relates to a reference value or cutoff value. The skilled person further understands that depending on the particular algorithm used to obtain the combined score, also a "low" score below a cut off or reference value can be indicative of benefit from a more aggressive therapy, e.g., cytotoxic chemotherapy. This is the case when genes having a positive correlation with high risk of metastasis factor into the algorithm with a positive coefficient, such that an overall high score indicates high expression of genes having a positive correlation with high risk.

According to an aspect of the invention there is provided a method as described above, wherein information regarding nodal status of the patient is processed in the step of mathematically combining expression level values for the genes to yield a combined score. According to an aspect of the invention there is provided a method as described above, wherein said information regarding nodal status is a numerical value ≤0 if said nodal status is negative and said information is a numerical value >0 if said nodal status positive or unknown. In exemplary embodiments of the invention a negative nodal status is assigned the value 0, an unknown nodal status is assigned the value 0.5 and a positive nodal status is assigned the value 1. Other values may be chosen to reflect a different weighting of the nodal status within an algorithm.

As described more fully in EP2553118, RNA levels of genes coding for specific combinations of the genes UBE2C, BRCS, DHCR7, STC2, AZGP1, RBBP8, IL6ST, and MGP, or specific combinations thereof, as indicated, can be determined. Mathematical mapping between the expression values of a gene can be used to replace that gene. For example:

According to the invention, this object is achieved by a method for predicting a response to and/or benefit of chemotherapy, including neoadjuvant chemotherapy, in a patient suffering from or at risk of developing recurrent neoplastic disease, in particular breast cancer, said method comprising the steps of:
(a) determining RNA expression level values of four or more of the following 8 genes in a tumor sample from the patient: UBE2C, BIRC5, DHCR7, STC2, AZGP1, RBBP8, IL6ST and MGP; or determining the RNA expression levels of four or more of the following 8 genes in a tumor sample from the patient: UBE2C, RACGAP1, DHCR7, STC2, AZGP1, RBBP8, IL6ST and MGP;
(b) generating an expression score by combining the expression level values for the genes of the mentioned set recited in (a);
(c) generating a clinical values score; and
(d) mathematically combining the expression score with the clinical values score to generate a combined score wherein the combined score is indicative of a prognosis for the patient.

In some embodiments the four or more genes are BIRC5, UBE2C, RBBP8, and IL6ST. Additional embodiments of the four or more genes can include any of the biomarker panels described in Table 1.

TABLE 1

| | |
|---|---|
| Panel 1 | BIRC5, UBE2C, RBBP8, and IL6ST |
| Panel 2 | BIRC5, UBE2C, RBBP8, IL6ST, and DHCR7 |
| Panel 3 | BIRC5, UBE2C, RBBP8, IL6ST, and AZGP1 |
| Panel 4 | BIRC5, UBE2C, RBBP8, IL6ST, and MGP |
| Panel 5 | BIRC5, UBE2C, RBBP8, IL6ST, and STC2 |
| Panel 6 | BIRC5, UBE2C, RBBP8, IL6ST, DHCR7, and AZGP1 |
| Panel 7 | BIRC5, UBE2C, RBBP8, IL6ST, DHCR7, and MGP |
| Panel 8 | BIRC5, UBE2C, RBBP8, IL6ST, DHCR7, and STC2 |
| Panel 9 | BIRC5, UBE2C, RBBP8, IL6ST, AZGP1, and MGP |
| Panel 10 | BIRC5, UBE2C, RBBP8, IL6ST, AZGP1, and STC2 |
| Panel 11 | BIRC5, UBE2C, RBBP8, IL6ST, MGP, and STC2 |
| Panel 12 | BIRC5, UBE2C, RBBP8, IL6ST, DHCR7, AZGP1, and MGP |
| Panel 13 | BIRC5, UBE2C, RBBP8, IL6ST, DHCR7, AZGP1, and STC |
| Panel 14 | BIRC5, UBE2C, RBBP8, IL6ST, DHCR7, MGP, and STC |
| Panel 15 | BIRC5, UBE2C, RBBP8, IL6ST, AZGP1, MGP, and STC |
| Panel 16 | BIRC5, UBE2C, RBBP8, IL6ST, DHCR7, AZGP1, MGP, and STC |

BIRC5 may be replaced by UBE2C or TOP2A or RACGAP1 or AURKA or NEK2 or E2F8 or PCNA or CYBRD1 or DCN or ADRA2A or SQLE or CXCL12 or EPHX2 or ASPH or PRSS16 or EGFR or CCND1 or TRIM29 or DHCR7 or PIP or TFAP2B or WNT5A or APOD or PTPRT with the proviso that after a replacement 8 different genes are selected; and UBE2C may be replaced by BIRC5 or RACGAP1 or TOP2A or AURKA or NEK2 or E2F8 or PCNA or CYBRD1 or ADRA2A or DCN or SQLE or CCND1 or ASPH or CXCL12 or PIP or PRSS16 or EGFR or DHCR7 or EPHX2 or TRIM29 with the proviso that after a replacement 8 different genes are selected; and DHCR7 may be replaced by AURKA, BIRC5, UBE2C or by any other gene that may replace BIRC5 or UBE2C with the proviso that after a replacement 8 different genes are selected; and STC2 may be replaced by INPP4B or IL6ST or SEC14L2 or MAPT or CHPT1 or ABAT or SCUBE2 or ESR1 or RBBP8 or PGR or PTPRT or HSPA2 or PTGER3 with the proviso that after a replacement 8 different genes are selected; and AZGP1 may be replaced by PIP or EPHX2 or PLAT or SEC14L2 or SCUBE2 or PGR with the proviso that after a replacement 8 different genes are selected; and RBBP8 may be replaced by CELSR2 or PGR or STC2 or ABAT or IL6ST with the proviso that after a replacement 8 different genes are selected; and IL6ST may be replaced by INPP4B or STC2 or MAPT or SCUBE2 or ABAT or PGR or SEC14L2 or ESR1 or GJA1 or MGP or EPHX2 or RBBP8 or PTPRT or PLAT with the proviso that after a replacement 8 different genes are selected; and MGP may be replaced by APOD or IL6ST or EGFR with the proviso that after a replacement 8 different genes are selected.

Deriving a Score

The methods of the invention are based on quantitative determination of RNA species isolated from the tumor in order to obtain expression values and subsequent bioinformatic analysis of said determined expression values. To determine an EP score, the relative RNA expression of the relevant genes is measured from the sample and quantified as described herein, and their measured values are used for calculation by means of a discriminate function.

The scores can determined using algorithms as described herein combined with clinical variables such as tumor size and nodal status. The clinical variables such as tumor size and nodal status can be determined by methods well known in the art. The scores can then be integrated to determine a risk score using statistical methodology that includes filling with a Cox proportional hazards regression model as described herein. A high score value may indicates a high risk for development of distant metastasis, a low score value may indicates a low risk of distant metastasis. Consequently, a high score also indicates that the patient is a high risk patient who will benefit from a more aggressive therapy, e.g., cytotoxic chemotherapy. Score values can be alternatively assigned for example, instead of a high score value indicating a high risk for development of distant metastasis, a low score value may indicate a high risk for development of distant metastasis and a high score value may indicate a low risk of distant metastasis.

For example, a score can be set such that a value is given a range from 0-6.0, and a difference between two scores would be a value of at least one point. The practitioner can then assign a risk score based on the values. For example, in some embodiments a score of 1 to 3.4 represents a low level of risk, and a score of 3.5 to 6.0 represents a high level of risk. The disease activity score can change based on the range of the score. The range can be expressed by any unit, for example, percentage points. For example, a 10-year likelihood of distant recurrence can be expressed in percentages such that a score, e.g., between 0 and 10 can represent low risk of distant recurrence. Numeric risk score values can further be correlated with 10-year likelihood of distant recurrence, e.g., on a risk score of range of 1-6.0, a low risk score of 2.6 can represent a 5% likelihood of distant recurrence, a risk score of 4.0 can represent a 15% change of distant recurrence, and a risk score of 5.0 can represent a 30% chance of distant recurrence, etc.

Expression Analysis

The methods of the invention are based on quantitative determination of RNA species isolated from the tumor in order to obtain expression values and subsequent bioinformatic analysis of said determined expression values.

Markers such as target polynucleotide molecules or proteins, can be extracted from a sample taken from an individual afflicted with a condition such as breast cancer. The markers might be isolated from any type of tumor sample, e.g., biopsy samples, smear samples, resected tumor material, fresh frozen tumor tissue or from paraffin embedded and formalin fixed tumor tissue. The sample may be collected in any clinically acceptable manner, but must be collected such that marker-derived polynucleotides (e.g., RNA) are preserved (if gene expression is to be measured) or proteins are preserved (if encoded proteins are to be measured). For example, mRNA or nucleic acids derived therefrom (e.g., cDNA or amplified DNA) are preferably labeled distinguishably from standard or control polynucleotide molecules, and both are simultaneously or independently hybridized to a microarray comprising some or all of the markers or marker sets or subsets described above. Alternatively, mRNA or nucleic acids derived therefrom may be labeled with the same label as the standard or control polynucleotide molecules, wherein the intensity of hybridization of each at a particular probe is compared. A sample may comprise any clinically relevant tissue sample, such as a tumor biopsy or fine needle aspirate, or a sample of bodily fluid, such as blood, plasma, serum, lymph, ascitic fluid, cystic fluid, urine or nipple exudate.

Expression can be measured using RT-PCR; e.g., polynucleotide primers specific for the differentially expressed biomarker mRNA sequences reverse-transcribe the mRNA into DNA, which is then amplified in PCR and can be visualized and quantified. Biomarker RNA can also be quantified using, for example, other target amplification methods, such as TMA, SDA, and NASBA, or signal amplification methods (e.g., bDNA), and the like. Ribonuclease protection assays can also be used, using probes that specifically recognize one or more biomarker mRNA sequences, to determine gene expression.

The measured value obtained upon performing RT-qPCR, which inversely correlates with the quantity of RNA present in the analyzed sample, can be a Ct value. It indicates after how many amplification cycles a sufficient amount of the PCR probe has been enzymatically degraded, so that the thus achieved reduction of the fluorescence quenching of the PCR dye by the PCR quencher is sufficient to be able to measure the fluorescence of the PCR dye. Therefore, a high Ct value in RT-qPCR is an indicator of a small amount of RNA to be analyzed in a sample.

The level of the Ct value can depend on the concentration of the analyzed RNA in the sample, and also primarily on the total amount of RNA in the sample. However, especially in the analysis of a tissue sample, it is difficult to precisely define the amount of analyzed tissue and thus to be able to calculate a concentration in the tissue. This is mainly because tissues are mostly heterogeneous. The water content above all, but also the lipid content or the proportion of non-cellular components, can vary significantly. Thus, variations in the analysis of the RNA amounts of different genes in human or animal tissue often reflect the variation of the amount of the cellular fraction of the tissue subjected to in the analysis rather than the biological differences between different tissue samples. In addition, the result of an RNA quantification is often substantially affected by the integrity of the RNA to be analyzed and by the amplification efficiency of the reagents employed. Therefore, the Ct values obtained in the RNA analysis of tissue are often primarily the product of different experimental factors, and to a lesser extent caused by the actually examined biological differences between the analyzed samples. Thus, if it is desired to measure the concentration of RNA in the cells of a tissue sample, the Ct value as a raw measured value of RT-qPCR might be unsuitable.

Therefore, in order to be able to compare the RNA concentrations in two different tissue samples in a reasonable way, the Ct values can be normalized on the basis of an invariant reference quantity. The obvious approach would be to normalize the Ct value on the basis of a particular amount of tissue, for example, one milligram or one microgram. However, because of the heterogeneity of the tissue, this method can be practicable only to a very limited degree and is rarely used. The most common method in RT-qPCR is the normalization of the Ct values of the analyzed RNA transcripts (genes of interest or GOI) on the basis of the Ct value of one or more other, invariant genes in the same sample. These invariant genes are mostly referred to as reference or normalization genes, sometimes also as "housekeeper genes." The invariance of the RNA expression of the normalization gene under the measuring conditions is the primary requirement demanded of a normalization gene. A variability of the amount of the RNA transcript of the normalization gene would reduce the purpose of normalization. A variant normalization gene has the consequence that the allegedly "normalized" Ct value of a "gene of interest" is actually not normalized. In this case, it depends on factors other than the transcript concentration of the gene of interest. Therefore, the normalization of a "gene of interest" using a variant gene or the correspondingly variant average of several non-variant genes might not be a normalization at all, because the correspondingly formed "two-gene ratio" does not allow conclusions to be made on the transcript quantity of the "gene of interest."

Because the invariance of a single gene can be difficult to ensure, the expression level of the RNA of several reasonably invariant genes can be averaged in practice, expecting that the average of these genes exhibits a lower biological variance than that of the RNA concentration of each individual normalization gene.

In any event, the RNA quantity of the "gene of interest" can be expressed relative to the RNA quantity of one invariant gene, to the average of the RNA quantities of some invariant genes, or to the average of a large number of arbitrarily chosen genes. This can be done by dividing the RNA quantity of the "gene of interest" by the quantity of RNA of the reference gene, or by the average of the RNA quantities of the reference genes. Because there can be a logarithmic relationship between the Ct value and the RNA quantity, the normalization can be then performed by subtracting the Ct values. This method is referred to as a delta-CT method. The normalized Ct value obtained is usually referred to as a delta-CT value.

In this way, the described EP score can be calculated in two steps from the Ct values of the RNA molecules measured for the determination of the EP score: at first, the eight informative genes are normalized against the average of three invariant reference genes, and then the delta-Ct values of the eight informative genes can be linearly combined. Alternative methods of normalizing an EP score are described in PT/EP2017/055601, which is hereby incorporated by reference in its entirety.

Alternatively, biomarker protein and nucleic acid metabolites can be measured by any method that is well known in the art. The term "metabolite" includes any chemical or biochem-ical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radio-chemical analysis, near-infrared spectroscopy (near-IR), nuclear magnetic resonance spectroscopy (NMR), light scattering analysis (LS), mass spectrometry, pyrolysis mass spectrometry, nephelome-try, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. See WO 04/056456 and WO 04/088309, each of which is hereby incorporated by reference in its entirety. In this regard, other biomarker analytes can be measured using the above-mentioned detection methods, or other methods known to the skilled artisan. For example, circulating calcium ions ($Ca^{2+}$) can be detected in a sample using fluorescent dyes such as the Fluo series, Fura-2A, Rhod-2, among others. Other biomarker metabolites can be similarly detected using reagents that are specifically designed or tailored to detect such metabolites.

Statistical Analysis

Established statistical algorithms and methods well-known in the art, useful as models or useful in designing predictive models and deriving scores, which can include but are not limited to: analysis of variants (ANOVA); Bayesian networks; boosting and Ada-boosting; bootstrap aggregating (or bagging) algorithms; decision trees classification techniques, such as Classification and Regression Trees (CART), boosted CART, Random Forest (RF), Recursive Partitioning Trees (RPART), and others; Curds and Whey (CW); Curds and Whey-Lasso; dimen-sion reduction methods, such as principal component analysis (PCA) and factor rotation or factor analysis; discriminant analysis, including Linear Discriminant Analysis (LDA), Eigengene Linear Discriminant Analysis (ELDA), and quadratic discriminant analysis; Discriminant Function Analysis (DFA); factor rotation or factor analysis; genetic algorithms; Hidden Markov Models; kernel based machine algorithms such as kernel density estimation, kernel partial least squares algorithms, kernel matching pursuit algorithms, kernel Fisher's discriminate analysis algorithms, and kernel principal components analysis algorithms; linear regression and generalized linear models, including or utilizing Forward Linear Stepwise Regression, Lasso (or LASSO) shrinkage and selection method, and Elastic Net regularization and selection method; glmnet (Lasso and Elastic Net-regularized generalized linear model); Logistic Regression (LogReg); meta-learner algorithms; nearest neighbor methods for classification or regression, e.g. Kth-nearest neighbor (KNN); non-linear regression or classification algorithms; neural networks; partial least square; rules based classifiers; shrunken centroids (SC); sliced inverse regression; Standard for the Exchange of Product model data, Application Interpreted Constructs (StepAIC); super principal component (SPC) regression; and, Support Vector Machines (SVM) and Recursive Support Vector Machines (RSVM), among others. Additionally, clustering algorithms as are known in the art can be useful in determining subject sub-groups.

Logistic Regression is the traditional predictive modeling method of choice for dichotomous response variables; e.g., treatment 1 versus treatment 2. It can be used to model both linear and non-linear aspects of the data variables and provides easily interpretable odds ratios.

Discriminant Function Analysis (DFA) uses a set of analytes as variables (roots) to discriminate between two or more naturally occurring groups. DFA is used to test analytes that are significantly different between groups. A forward step-wise DFA can be used to select a set of analytes that maximally discriminate among the groups studied. Specifically, at each step all variables can be reviewed to determine which will maximally discriminate among groups. This information is then included in a discriminative function, denoted a root, which is an equation consisting of linear combinations of analyte concentrations for the prediction of group membership. The discriminatory potential of the final equation can be observed as a line plot of the root values obtained for each group. This approach identifies groups of analytes whose changes in concentration levels can be used to delineate profiles, diagnose and assess therapeutic efficacy. The DFA model can also create an arbitrary score by which new subjects can be classified as either "healthy" or "diseased." To facilitate the use of this score for the medical community the score can be rescaled so a value of 0 indicates a healthy individual and scores greater than 0 indicate increasing disease activity.

Classification and regression trees (CART) perform logical splits (if/then) of data to create a decision tree. All observations that fall in a given node are classified according to the most common outcome in that node. CART results are easily interpretable—one follows a series of if/then tree branches until a classification results.

Support vector machines (SVM) classify objects into two or more classes. Examples of classes include sets of treatment alternatives, sets of diagnostic alternatives, or sets of prognostic alternatives. Each object is assigned to a class based on its similarity to (or distance from) objects in the training data set in which the correct class assignment of each object is known. The measure of similarity of a new object to the known objects is determined using support vectors, which define a region in a potentially high dimensional space (>R6).

The process of bootstrap aggregating, or "bagging," is computationally simple. In the first step, a given dataset is randomly resampled a specified number of times (e.g., thousands), effectively providing that number of new datasets, which are referred to as "bootstrapped resamples" of data, each of which can then be used to build a model. Then, in the example of classification models, the class of every new observation is predicted by the number of classification models created in the first step. The final class decision is based upon a "majority vote" of the classification models; i.e., a final classification call is determined by counting the number of times a new observation is classified into a given group, and taking the majority classification (33%+ for a three-class system). In the example of logistical regression models, if a logistical regression is bagged 1000 times, there will be 1000 logistical models, and each will provide the probability of a sample belonging to class 1 or 2.

Curds and Whey (CW) using ordinary least squares (OLS) is another predictive modeling method. See L. Breiman and J H Friedman, *J. Royal. Stat. Soc. B* 1997, 59(1):3-54. This method takes advantage of the correlations between response variables to improve predictive accuracy, compared with the usual procedure of performing an individual regression of each response variable on the common set of predictor variables X. In CW, Y=XB*S, where Y=$(y_{kj})$ with k for the $k^{th}$ patient and j for $j^{th}$ response (j=1 for TJC, j=2 for SJC, etc.), B is obtained using OLS, and S is the shrinkage matrix computed from the canonical coordinate system. Another method is Curds and Whey and Lasso in combination (CW-Lasso). Instead of using OLS to obtain B, as in CW, here Lasso is used, and parameters are adjusted accordingly for the Lasso approach.

Many of these techniques are useful either combined with a biomarker selection technique (such as, for example, forward selection, backwards selection, or stepwise selection), or for complete enumeration of all potential panels of a given size, or genetic algorithms, or they can themselves include biomarker selection methodologies in their own techniques. These techniques can be coupled with information criteria, such as Akaike's Information Criterion (AIC), Bayes Information Criterion (BIC), or cross-validation, to quantify the tradeoff between the inclusion of additional biomarkers and model improvement, and to minimize overfit. The resulting predictive models can be validated in other studies, or cross-validated in the study they were originally trained in, using such techniques as, for example, Leave-One-Out (LOO) and 10-Fold cross-validation (10-Fold CV).

According to an aspect of the invention there is provided a method as described above, wherein information regarding tumor size is processed in the step of mathematically combining expression level values for the genes to yield a combined score.

The invention further relates to a computer program product capable of processing values representative of an expression level of a combination of genes mathematically combining said values to yield a combined score, wherein said combined score is indicative of efficacy or benefit from chemotherapy of said patient, according to the above methods. Said computer program product may be stored on a data carrier or implemented on a diagnostic system capable of outputting values representative of an expression level of a given gene, such as a real time PCR system. If the computer program product is stored on a data carrier or running on a computer, operating personal can input the expression values obtained for the expression level of the respective genes. The computer program product can then apply an algorithm to produce a combined score indicative of benefit from cytotoxic chemotherapy for a given patient.

Generating a Score that Includes Clinical Variables

A score according to the present invention can include clinical variables. Such variables can be included through a variety of methods well known to the skilled artisan. For examples, and algorithm EPclin (score $s_{clin}$) including its threshold to discriminate low risk from high risk can be constructed based on the training data set. Biomarker expression determination can be the most significant variable and selected first, then nodal status, then tumor size. An exemplary algorithm including variables can be, for example:

$$s_{clin}=0.35t+0.64n+0.28s$$

where t codes for tumor size (1: ≤1 cm, 2: >1 cm to ≤2 cm, 3: >2 cm to ≤5 cm, 4: >5 cm) and n for nodal status (1: negative, 2: 1 to 3 positive nodes, 3: 4 to 10 positive nodes, 4: >10 positive nodes).

The threshold can be designed to correspond to a 10% probability of developing a distant recurrence within 10 years after surgery. To numerically calculate the threshold, a model associating the EPclin score to the probability of distant recurrence can be constructed. Based on such models, a threshold can be determined to be 3.3.

Predicting Benefit

Based on these expression values a prognostic score is calculated by a mathematical combination. Following expression value determination combined with clinical variables such as tumor size and nodal status, an individual is classified into a condition subset and a prognosis is made based on the EPclin score derived from the combination of expression and clinical variable scores. The individual's responsiveness to chemotherapy and the benefit derived from such chemotherapy is then determined based on the individual's classification and prognosis of chemotherapy benefit.

The present invention can further include different types of benefits, e.g., absolute and relative benefits. Absolute benefit is the reduction in the risk of distant metastasis. For example, if the risk of distant metastasis is 20% without chemotherapy and 15% with chemotherapy, then the absolute benefit is 5% (20%-15%). In contrast, relative benefit is the relative reduction in the risk of distance metastasis that is the absolute benefit divided by the risk without chemotherapy. Applying the relative benefit example above, the relative benefit would be 25% (5% divided by 20%).

Any number of proportional hazard models as known in the art, which can be used to predict a chemotherapy benefit. Many outcomes can be used as a covariate associated with the hazard, such as distant metastasis. Proportional hazard model well known in the art, which include but is not limited to, Cox and poisson models. The Cox proportional hazards regression model can model the impact of variables, such as chemotherapy, on the survival probability time to metastases or distant recurrence. A Cox proportional hazards model analysis can be used, which is a regression method for survival data that provides an estimate of the hazard ratio and its confidence interval. The Cox model is a well-recognized statistical technique for exploring the relationship between the survival of a patient and particular variables. The statistical method permits estimation of the hazard (i.e., risk) of individuals given their prognostic variables (e.g., intrinsic gene expression profile with or without additional clinical factors such as tumor size and nodal status). The "hazard ratio" is the risk of death, or metastases, at any given time point for patients displaying particular prognostic variables. See generally Spruance et al., Antimicrob. Agents & Chemo. 48:2787-92 (2004).

Therapeutic Regimens

The present invention provides methods of recommending therapeutic regimens, e.g., chemotherapy regimens, including withdrawal from therapeutic regiments, following the determination of differences in expression of the biomarkers and clinical variables disclosed herein. Measuring scores derived from expression levels of the biomarkers and clinical variables disclosed herein over a period time can provide a clinician with a dynamic picture of a subject's biological state. These embodiments of the present teachings thus will provide subject-specific biological information, which will be informative for therapy decision and will facilitate therapy response monitoring, and should result in more rapid and more optimized treatment, better control of disease activity, and an increase in the proportion of subjects achieving remission.

Reference Standards for Treatment

In many embodiments, the levels of one or more analyte biomarkers or the levels of a specific panel of analyte biomarkers in combination with clinical variables in a sample are compared to a reference standard ("reference standard" or "reference level") in order to direct treatment decisions. Expression levels of the one or more biomarkers and clinical variables can be combined into a score, which can represent chemotherapy benefit. The reference standard used for any embodiment disclosed herein may comprise average, mean, or median levels of the one or more analyte biomarkers or the levels of the specific panel of analyte biomarkers and clinical variables in a control population. The reference standard may further include an earlier time point for the same subject. For example, a reference standard may include a first time point, and the levels of the one or more analyte biomarkers and clinical variables can be examined again at second, third, fourth, fifth, sixth time points, etc. Any time point earlier than any particular time point can be considered a reference standard. The reference standard may additionally comprise cutoff values or any other statistical attribute of the control population, or earlier time points of the same subject, such as a standard deviation from the mean levels of the one or more analyte biomarkers or the levels of the specific panel of analyte biomarkers and clinical variables. In some embodiments, the control population may comprise healthy individuals or the same subject prior to the administration of any therapy.

In some embodiments, a score may be obtained from the reference time point, and a different score may be obtained from a later time point. A first time point can be when an initial chemotherapeutic regimen is begun. A first time point can also be when a first assay is performed. A time point can be hours, days, months, years, etc. In some embodiments, a time point is one month. In some embodiments, a time point is two months. In some embodiments, a time point is three months. In some embodiments, a time point is four months. In some embodiments, a time point is five months. In some embodiments, a time point is six months. In some embodiments, a time point is seven months. In some embodiments, a time point is eight months. In some embodiments, a time point is nine months. In some embodiments, a time point is ten months. In some embodiments, a time point is eleven months. In some embodiments, a time point is twelve months. In some embodiments, a time point is two years. In some embodiments, a time point is three years. In some embodiments, a time point is four years. In some embodiments, a time point is five years. In some embodiments, a time point is ten years.

A difference in the score can be interpreted as a decrease in disease activity or decrease in chemotherapy benefit. For example, lower score can indicate a lower level of disease activity, or remission. In these circumstances a second score having a lower score than the reference score, or first score, means that the subject's disease activity has been lowered (improved) between the first and second time periods, or is in remission. Alternatively, a higher score can indicate a lower level of disease activity, or remission. In these circumstances, a second score having a higher score than the reference score, or first score, also means that the subject's disease activity has improved between the first and second time periods, or is in remission.

A difference in the score can also be interpreted as an increase in disease activity or metastasis, or increased chemotherapy benefit. For example, lower score can indicate a higher level of disease activity, or metastasis, or decreased chemotherapy benefit. In these circumstances a second score having a lower score than the reference score, or first score, means that the subject's disease activity has been increased (worsened) between the first and second time periods. Alternatively, a higher score can indicate a higher level of disease activity, or metastasis. In these circumstances, a second score having a higher score than the reference score, or first score, also means that the subject's disease activity has worsened between the first and second time periods, or is metastasizing, or increased benefit from chemotherapy.

The differences can be variable. For example, when a difference in the score is interpreted as a decrease in disease activity or chemotherapy benefit, a large difference can mean a greater decrease in disease activity than a lower or moderate difference. Alternatively, when a difference in the score is interpreted as an increase in disease activity or chemotherapy benefit, a large difference can mean a greater increase in disease activity than a lower or moderate difference.

In many embodiments, the levels of one or more analyte biomarkers or the levels of a specific panel of analyte biomarkers and clinical variables in a sample are compared to a reference standard ("reference standard" or "reference level") in order to direct treatment decisions. Expression levels of the one or more biomarkers can be combined into a score, which can represent disease activity or benefit from chemotherapy. The reference standard used for any embodiment disclosed herein may comprise average, mean, or median levels of the one or more analyte biomarkers or the levels of the specific panel of analyte biomarkers and clinical variables in a control population. The reference standard may further include an earlier time point for the same subject. For example, a reference standard may include a first time point, and the levels of the one or more analyte biomarkers can be examined again at second, third, fourth, fifth, sixth time points, etc. Any time point earlier than any particular time point can be considered a reference standard. The reference standard may additionally comprise cutoff values or any other statistical attribute of the control population, or earlier time points of the same subject, such as a standard deviation from the mean levels of the one or more analyte biomarkers or the levels of the specific panel of analyte biomarkers and clinical variables. In some embodiments, the control population may comprise healthy individuals or the same subject prior to the administration of any therapy.

In some embodiments, a score may be obtained from the reference time point, and a different score may be obtained from a later time point. A first time point can be when an initial therapeutic regimen is begun. A first time point can also be when a first immunoassay is performed. A time point can be hours, days, months, years, etc. In some embodiments, a time point is one month. In some embodiments, a time point is two months. In some embodiments, a time point is three months. In some embodiments, a time point is four months. In some embodiments, a time point is five months. In some embodiments, a time point is six months. In some embodiments, a time point is seven months. In some embodiments, a time point is eight months. In some embodiments, a time point is nine months. In some embodiments, a time point is ten months. In some embodiments, a time point is eleven months. In some embodiments, a time point is twelve months. In some embodiments, a time point is two years. In some embodiments, a time point is three years. In some embodiments, a time point is four years. In some embodiments, a time point is five years. In some embodiments, a time point is ten years.

A difference in the score can be interpreted as a decrease in disease activity or decrease in chemotherapy benefit. For example, lower score can indicate a lower level of disease activity, or remission, or chemotherapy benefit. In these circumstances a second score having a lower score than the reference score, or first score, means that the subject's disease activity has been lowered (improved) between the first and second time periods, or is in remission, or less chemotherapy benefit. Alternatively, a higher score can indicate a lower level of disease activity, or remission, or less chemotherapy benefit. In these circumstances, a second score having a higher score than the reference score, or first score, also means that the subject's disease activity has improved between the first and second time periods, or is in remission, or less chemotherapy benefit.

A difference in the score can also be interpreted as an increase in disease activity or increased chemotherapy benefit. For example, lower score can indicate a higher level of disease activity, or metastasis, or increased chemotherapy benefit. In these circumstances a second score having a lower score than the reference score, or first score, means that the subject's disease activity has been increased (worsened) between the first and second time periods. Alternatively, a higher score can indicate a higher level of disease activity, or metastasis, or increased chemotherapy benefit. In these circumstances, a second score having a higher score than the reference score, or first score, also means that the subject's disease activity has worsened between the first and second time periods, or is metastasizing.

The differences can be variable. For example, when a difference in the score is interpreted as a decrease in disease activity or chemotherapy benefit, a large difference can mean a greater decrease in disease activity than a lower or moderate difference. Alternatively, when a difference in the score is interpreted as an increase in disease activity, a large difference can mean a greater increase in disease activity or chemotherapy benefit than a lower or moderate difference.

Reference Therapy for Treatment

In some embodiments, a patient is treated more or less aggressively than a reference therapy based on the difference of scores. A reference therapy is any therapy that is the standard of care for the disease. The standard of care can vary temporally and geographically, and a skilled person can easily determine the appropriate standard of care by consulting the relevant medical literature.

In some embodiments, a more aggressive therapy than the standard therapy comprises beginning treatment earlier than in the standard therapy. In some embodiments, a more aggressive therapy than the standard therapy comprises administering additional treatments than in the standard therapy. In some embodiments, a more aggressive therapy than the standard therapy comprises treating on an accelerated schedule compared to the standard therapy. In some embodiments, a more aggressive therapy than the standard therapy comprises administering additional treatments not called for in the standard therapy.

In some embodiments, a less aggressive therapy than the standard therapy comprises delaying treatment relative to the standard therapy. In some embodiments, a less aggressive therapy than the standard therapy comprises administering less treatment than in the standard therapy. In some embodiments, a less aggressive therapy than the standard therapy comprises administering treatment on a decelerated schedule compared to the standard therapy. In some embodiments, a less aggressive therapy than the standard therapy comprises administering no treatment.

Chemotherapy Treatments

In one embodiment, the practitioner discontinues a therapy regimen if a score is low. In one embodiment, the practitioner does not change the therapy regimen if the score is high. In one embodiment, the practitioner adjusts the therapy based on a comparison between difference scores, or based on an initial predictive score. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In one embodiment a less aggressive therapy comprises no change in the therapy regimen. In one embodiment a less aggressive therapy comprises delaying treatment. In one embodiment a less aggressive therapy comprises selecting and administering less potent drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy. In one embodiment, more aggressive therapy comprises selecting and administering more potent drugs, increasing drug dosage, accelerating dose schedule, and increasing length of therapy. In some embodiments, a more aggressive therapy comprises administering a combination of drug-based therapies, non-drug-based therapies, or a combination of classes of drug-based therapies.

Therapies can include neoadjuvant or adjuvant therapy. Adjuvant therapy may include chemotherapy (the use of drugs to kill cancer cells) and/or radiation therapy (the use of high energy x-rays to kill cancer cells).

Chemotherapy can be performed using any one or a combination of the anti-cancer therapies known in the art, including but not limited to topoisomerase inhibitors, DNA binding agents, anti-metabolites, ionizing radiation, or a combination of known DNA damaging agents.

A topoisomerase inhibitor that can be used in conjunction with the invention can be a topoisomerase I (Topo I) inhibitor, a topoisomerase II (Topo II) inhibitor, or a dual topoisomerase I and II inhibitor. A topo I inhibitor can be from any of the following classes of compounds: camptothecin analogue (e.g., karenitecin, aminocamptothecin, lurtotecan, topotecan, irinotecan, BAY 56-3722, rubitecan, GI14721, exatecan mesylate), rebeccamycin analogue, PNU 166148, rebeccamycin, TAS-103, camptothecin (e.g., camptothecin polyglutamate, camptothecin sodium), intoplicine, ecteinascidin 743, J-107088, pibenzimol. Examples of preferred topo I inhibitors include but are not limited to camptothecin, topotecan (hycaptamine), irinotecan (irinotecan hydrochloride), belotecan, or an analogue or derivative thereof. A topo II inhibitor that can be used in conjunction with the invention can be from any of the following classes of compounds: anthracycline antibiotics (e.g., carubicin, pirarubicin, daunorubicin citrate liposomal, daunomycin, 4-iodo-4-doxydoxorubicin, doxorubicin, n,n-dibenzyl daunomycin, morpholinodoxorubicin, aclacinomycin antibiotics, duborimycin, menogaril, nogalamycin, zorubicin, epirubicin, marcellomycin, detorubi-cin, annamycin, 7-cyanoquinocarcinol, deoxydoxorubicin, idarubicin, GPX-100, MEN-10755, vairubicin, KRN5500), epipodophyllotoxin compound (e.g., podophyllin, teniposide, etoposide, GL331, 2-ethylhydrazide), anthraquinone compound (e.g., ametantrone, bisantrene, mitoxantrone, anthraquinone), ciprofloxacin, acridine carboxamide, amonafide, anthrapyrazole antibiotics (e.g., teloxantrone, sedoxantrone trihydrochloride, piroxantrone, anthrapyrazole, losoxantrone), TAS-103, fostriecin, razoxane, XK469R, XK469, chloroquinoxaline sulfonamide, merbarone, intoplicine, elsamitrucin, CI-921, pyrazoloacridine, elliptinium, amsacrine. Examples of preferred topo II inhibitors include but are not limited to doxorubicin (Adriamycin), etoposide phosphate (etopofos), teniposide, sobuzoxane, or an analogue or derivative thereof.

DNA binding agents that can be used in conjunction with the invention include but are not limited to DNA groove binding agent, e.g., DNA minor groove binding agent; DNA crosslinking agent; intercalating agent; and DNA adduct forming agent. A DNA minor groove binding agent can be an anthracycline antibiotic, mitomycin antibiotic (e.g., porfiromycin, KW-2149, mitomycin B, mitomycin A, mitomycin C), chromomycin A3, carzelesin, actinomycin antibiotic (e.g., cactinomycin, dactinomycin, actinomycin Fl), brostallicin, echinomycin, bizelesin, duocarmycin antibiotic (e.g., KW 2189), adozelesin, olivomycin antibiotic, plicamycin, zinostatin, distamycin, MS-247, ecteinascidin 743, amsacrine, anthramycin, and pibenzimol, or an analogue or derivative thereof.

DNA crosslinking agents include but are not limited to antineoplastic alkylating agent, methoxsalen, mitomycin antibiotic, psoralen. An antineoplastic alkylating agent can be a nitrosourea compound (e.g., cystemustine, tauromustine, semustine, PCNU, streptozocin, SarCNU, CGP-6809, carmustine, fotemustine, methylnitrosourea, nimustine, ranimustine, ethylnitrosourea, lomustine, chlorozotocin), mustard agent (e.g., nitrogen mustard compound, such as spiromustine, trofosfamide, chlorambucil, estramustine, 2,2,2-trichlorotriethylamine, prednimustine, novem-bichin, phenamet, glufosfamide, peptichemio, ifosfamide, defosfamide, nitrogen mustard, phenesterin, mannomustine, cyclophosphamide, melphalan, perfosfamide, mechlorethamine oxide hydrochloride, uracil mustard, bestrabucil, DHEA mustard, tallimustine, mafosfamide, aniline mustard, chlornaphazine; sulfur mustard compound, such as bischloroethylsulfide; mustard prodrug, such as TLK286 and ZD2767), ethylenimine compound (e.g., mitomycin antibiotic, ethylenimine, uredepa, thiotepa, diaziquone, hexamethylene bisacetamide, pentamethylmelamine, altretamine, carzinophilin, triaziquone, meturedepa, benzodepa, carboquone), alkylsulfonate compound (e.g., dimethylbusulfan, Yoshi-864, improsulfan, piposulfan, treosulfan, busulfan, hepsulfam), epoxide compound (e.g., anaxirone, mitolactol, dianhydrogalactitol, teroxirone), miscellaneous alkylating agent (e.g., ipomeanol, carzelesin, methylene dimethane sulfonate, mitobronitol, bizelesin, adozelesin, piperazinedione, VNP40101M, asaley, 6-hydroxymethylacylfulvene, E09, etoglucid, ecteinascidin 743, pipobroman), platinum compound (e.g., ZD0473, liposomal-cisplatin analogue, satraplatin, BBR 3464, spiroplatin, ormaplatin, cisplatin, oxaliplatin, carboplatin, lobaplatin, zeniplatin, iproplatin), triazene compound (e.g., imidazole mustard, CB 10-277, mitozolomide, temozolomide, procarbazine, dacarbazine), picoline compound (e.g., penclomedine), or an analogue or derivative thereof. Examples of preferred alkylating agents include but are not limited to cisplatin, dibromodulcitol, fotemustine, ifosfamide (ifosfamid), ranimustine (ranomustine), nedaplatin (latoplatin), bendamustine (bendamustine hydrochloride), eptaplatin, temozolomide (methazolastone), carboplatin, altretamine (hexamethylmelamine), prednimustine, oxaliplatin (oxalaplatinum), carmustine, thiotepa, leusulfon (busulfan), lobaplatin, cyclophosphamide, bisulfan, melphalan, and chlorambucil, or analogues or derivatives thereof.

Intercalating agents can be an anthraquinone compound, bleomycin antibiotic, rebeccamycin analogue, acridine, acridine carboxamide, amonafide, rebeccamycin, anthrapyrazole antibiotic, echinomycin, psoralen, LU 79553, BW A773U, crisnatol mesylate, benzo(a)pyrene-7,8-diol-9,10-epoxide, acodazole, elliptinium, pixantrone, or an analogue or derivative thereof.

DNA adduct forming agents include but are not limited to enediyne antitumor antibiotic (e.g., dynemicin A, esperamicin A1, zinostatin, dynemicin, calicheamicin gamma II), platinum compound, carmustine, tamoxifen (e.g., 4-hydroxy-tamoxifen), psoralen, pyrazine diazohydroxide, benzo(a)pyrene-7,8-diol-9,10-epoxide, or an analogue or derivative thereof. Anti-metabolites include but are not limited to cytosine, arabinoside, floxuridine, fluorouracil, mercapto-purine, Gemcitabine, and methotrexate (MTX).

In an embodiment adjuvant chemotherapy treatments can include a regimen of 5-fluorouracil, epirubicin, and cyclophosphamide (FEC) with FEC followed by weekly paclitaxel (FEX-P), and then followed by 5-year hormonal therapy (tamoxifen, aromatase inhibitors, or both).

Kits

Other embodiments of the present teachings comprise biomarker detection reagents packaged together in the form of a kit for conducting any of the assays of the present teachings. In certain embodiments, the kits comprise oligonucleotides that specifically identify one or more biomarker nucleic acids based on homology and/or complementarity with biomarker nucleic acids. The oligonucleotide sequences may correspond to fragments of the biomarker nucleic acids. For example, the oligonucleotides can be more than 200, 200, 150, 100, 50, 25, 10, or fewer than 10 nucleotides in length. In other embodiments, the kits comprise antibodies to proteins encoded by the biomarker nucleic acids. The kits of the present teachings can also comprise aptamers. The kit can contain in separate containers a nucleic acid or antibody (the antibody either bound to a solid matrix, or packaged separately with reagents for binding to a matrix), control formulations (positive and/or negative), and/or a detectable label, such as but not limited to fluorescein, green fluorescent protein, rhodamine, cyanine dyes, Alexa dyes, luciferase, and radiolabels, among others. Instructions for carrying out the assay, including, optionally, instructions for generating a score, can be included in the kit; e.g., written, tape, VCR, or CD-ROM. The assay can for example be in the form of a Northern hybridization or a sandwich ELISA as known in the art.

In some embodiments of the present teachings, biomarker detection reagents can be immobilized on a solid matrix, such as a porous strip, to form at least one biomarker detection site. In some embodiments, the measurement or detection region of the porous strip can include a plurality of sites containing a nucleic acid. In some embodiments, the test strip can also contain sites for negative and/or positive controls. Alternatively, control sites can be located on a separate strip from the test strip. Optionally, the different detection sites can contain different amounts of immobilized nucleic acids, e.g., a higher amount in the first detection site and lesser amounts in subsequent sites. Upon the addition of test sample, the number of sites displaying a detectable signal provides a quantitative indication of the amount of biomarker present in the sample. The detection sites can be configured in any suitably detectable shape and can be, e.g., in the shape of a bar or dot spanning the width of a test strip.

In other embodiments of the present teachings, the kit can contain a nucleic acid substrate array comprising one or more nucleic acid sequences. The nucleic acids on the array specifically identify one or more nucleic acid sequences represented by the markers. In various embodiments, the expression of one or more of the sequences represented by the markers can be identified by virtue of binding to the array. In some embodiments the substrate array can be on a solid substrate, such as what is known as a "chip." See, e.g., U.S. Pat. No. 5,744,305. In some embodiments the substrate array can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

Machine-Readable Storage Medium

A machine-readable storage medium can comprise, for example, a data storage material that is encoded with machine-readable data or data arrays. The data and machine-readable storage medium are capable of being used for a variety of purposes, when using a machine programmed with instructions for using said data. Such purposes include, without limitation, storing, accessing and manipulating information relating to the disease activity of a subject or population over time, or disease activity in response to disease treatment, or for drug discovery for disease, etc. Data comprising measurements of the biomarkers of the present teachings, and/or the evaluation of disease activity or disease state from these biomarkers, can be implemented in computer programs that are executing on programmable computers, which comprise a processor, a data storage system, one or more input devices, one or more output devices, etc. Program code can be applied to the input data to perform the functions described herein, and to generate output information. This output information can then be applied to one or more output devices, according to methods well-known in the art. The computer can be, for example, a personal computer, a microcomputer, or a workstation of conventional design.

The computer programs can be implemented in a high-level procedural or object-oriented programming language, to communicate with a computer system. The programs can also be implemented in machine or assembly language. The programming language can also be a compiled or interpreted language. Each computer program can be stored on storage media or a device such as ROM, magnetic diskette, etc., and can be readable by a programmable computer for configuring and operating the computer when the storage media or device is read by the computer to perform the described procedures. Any health-related data management systems of the present teachings can be considered to be implemented as a computer-readable storage medium, configured with a computer program, where the storage medium causes a computer to operate in a specific manner to perform various functions, as described herein.

The biomarkers disclosed herein can be used to generate a "subject biomarker profile" taken from subjects who have a disease. The subject biomarker profiles can then be compared to a reference biomarker profile, in order to diagnose or identify subjects with disease, to monitor the progression or rate of progression of disease, or to monitor the effectiveness of treatment for a disease. The biomarker profiles, reference and subject, of embodiments of the present teachings can be contained in a machine-readable medium, such as analog tapes like those readable by a CD-ROM or USB flash media, among others. Such machine-readable media can also contain additional test results, such as measurements of clinical parameters and clinical assessments. The machine-readable media can also comprise subject information; e.g., the subject's medical or family history. The machine-readable media can also contain information relating to other disease activity algorithms and computed scores or indices, such as those described herein.

EXAMPLES

Aspects of the present teachings can be further understood in light of the following examples, which should not be construed as limiting the scope of the present teachings in any way.

Example 1—Combining EndoPredict with Clinical Variables

This example demonstrates the use of EndoPredict® in combination with clinical variables, including nodal status and tumor size, to predict the relative benefit of chemotherapy. The score derived from the combination of EndoPredict with nodal status and tumor size is referred to as "EPclin."

Methods

Two datasets were used to show that EPclin score predicts relative benefit of adjuvant chemotherapy. The first dataset is 1120 patients from the ABCSG-8 cohort, each patient of which was treated without adjuvant chemotherapy. The ABCSG-8 cohort had patients treated with adjuvant endocrine therapy only consisting of tamoxifen for either 5 or 2 years followed by anastrozole for 3 years). The ABCSG-8 samples were ER+, HER2-, node negative or positive (0-3 positive lymph nodes). There ABCSG-8 cohort included 69 samples with distant recurrence and 1051 samples with no distant recurrence. The second dataset is 555 patients from the GEICAM cohort, each patient of which was treated with adjuvant chemotherapy. The GEICAM cohort had patients treated with an adjuvant chemotherapy regimen of 5-fluorouracil, epirubicin, and cyclophosphamide (FEC) with FEC followed by weekly paclitaxel (FEX-P), and then followed by 5-year hormonal therapy (tamoxifen, aromatase inhibitors, or both). The GEICAM samples were ER+, HER2-, node positive. The GEICAM study samples with 1-3 positive nodes included 53 samples with distant recurrence and 304 samples with no distant recurrence. The GEICAM study samples with >3 positive nodes included 54 samples with distant recurrence and 144 samples with no distant recurrence.

The two datasets were combined and then analyzed using Cox PH modeling with distant metastasis as the outcome. The explanatory variables included EPclin score, treatment (chemotherapy vs no chemotherapy), and the interaction between treatment and EPclin score. The significance of the interaction term was evaluated using likelihood ration statistics.

The two datasets were further analyzed in node-positive patients only (ABCSG N=537, GEICAM N=555). The two datasets were combined and then analyzed using Cox PH modeling with distant metastasis as the outcome.

Results

The resulting p-value for the interaction between EPclin score and treatment for all samples was 0.0063. The hazard ratio for the interaction term for all samples was HR=0.64. The resulting p-value for the interaction between EPclin score and treatment in node-positive only samples was 0.0042, and the hazard ratio was HR=0.66. The chemotherapy benefit by EndoPredict risk groups is illustrated in Table 2.

TABLE 2

| | All patients | | | Low risk by EndoPredict | | | High risk by EndoPredict | | |
|---|---|---|---|---|---|---|---|---|---|
| | Risk without chemo | Absolute benefit | Relative benefit | Risk without chemo | Absolute benefit | Relative benefit | Risk without chemo | Absolute benefit | Relative benefit |
| Using All GEICAM patients | 10.0% | −1.1% | −11% | 5.0% | −2.9% | −58% | 18.3% | 1.7% | 10% |

TABLE 2-continued

| | All patients | | | Low risk by EndoPredict | | | High risk by EndoPredict | | |
|---|---|---|---|---|---|---|---|---|---|
| | Risk without chemo | Absolute benefit | Relative benefit | Risk without chemo | Absolute benefit | Relative benefit | Risk without chemo | Absolute benefit | Relative benefit |
| Using GEICAM patients with 1-3 pos. nodes | 10.0% | 0.7% | 7% | 5.0% | 0.7% | −14% | 18.3% | 3.0% | 16% |

Figure 2:
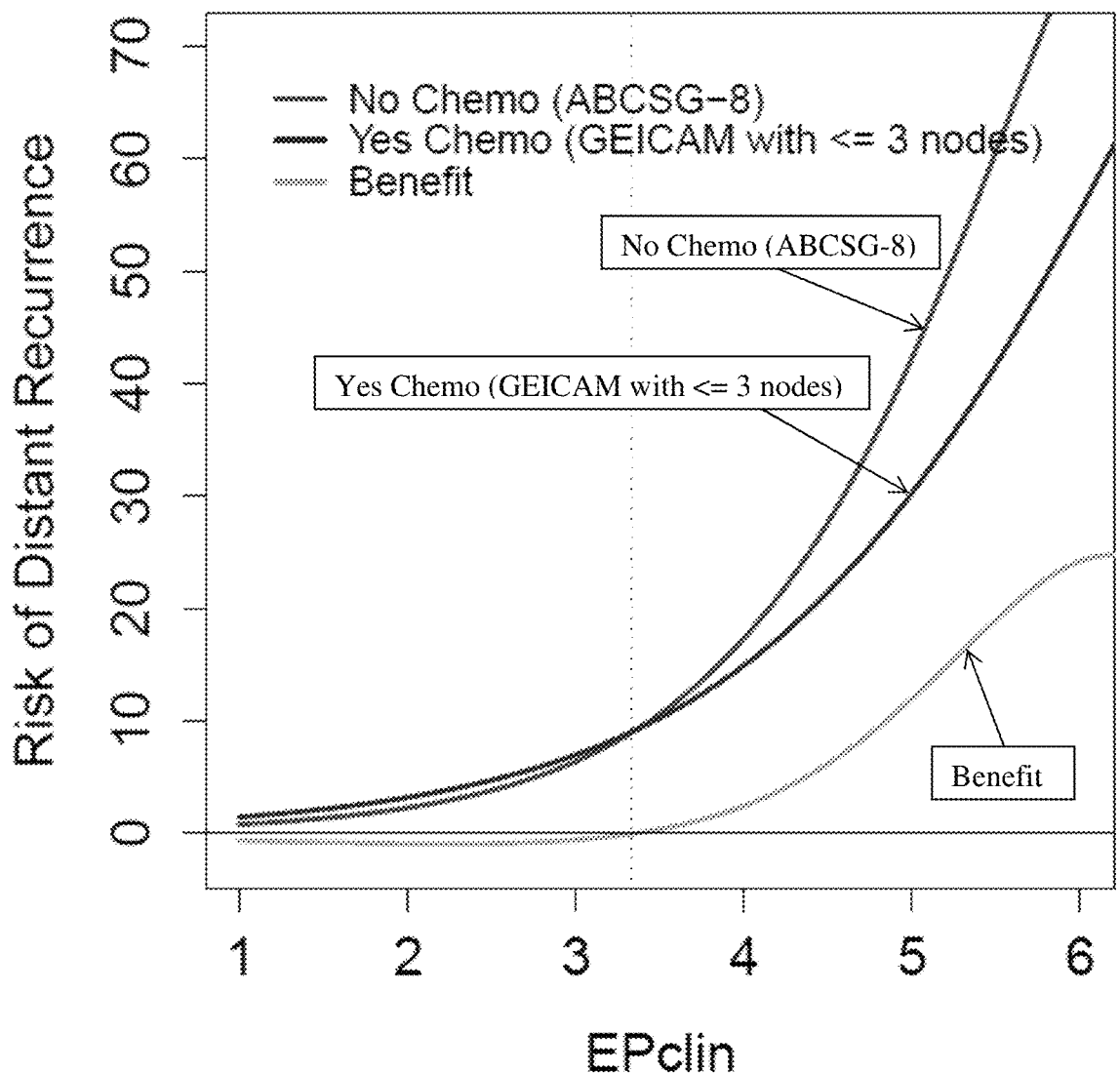
FIG. 2 demonstrates the use of EPclin to predict the benefit of chemotherapy in samples with 1-3 positive nodes.
Figure 3:
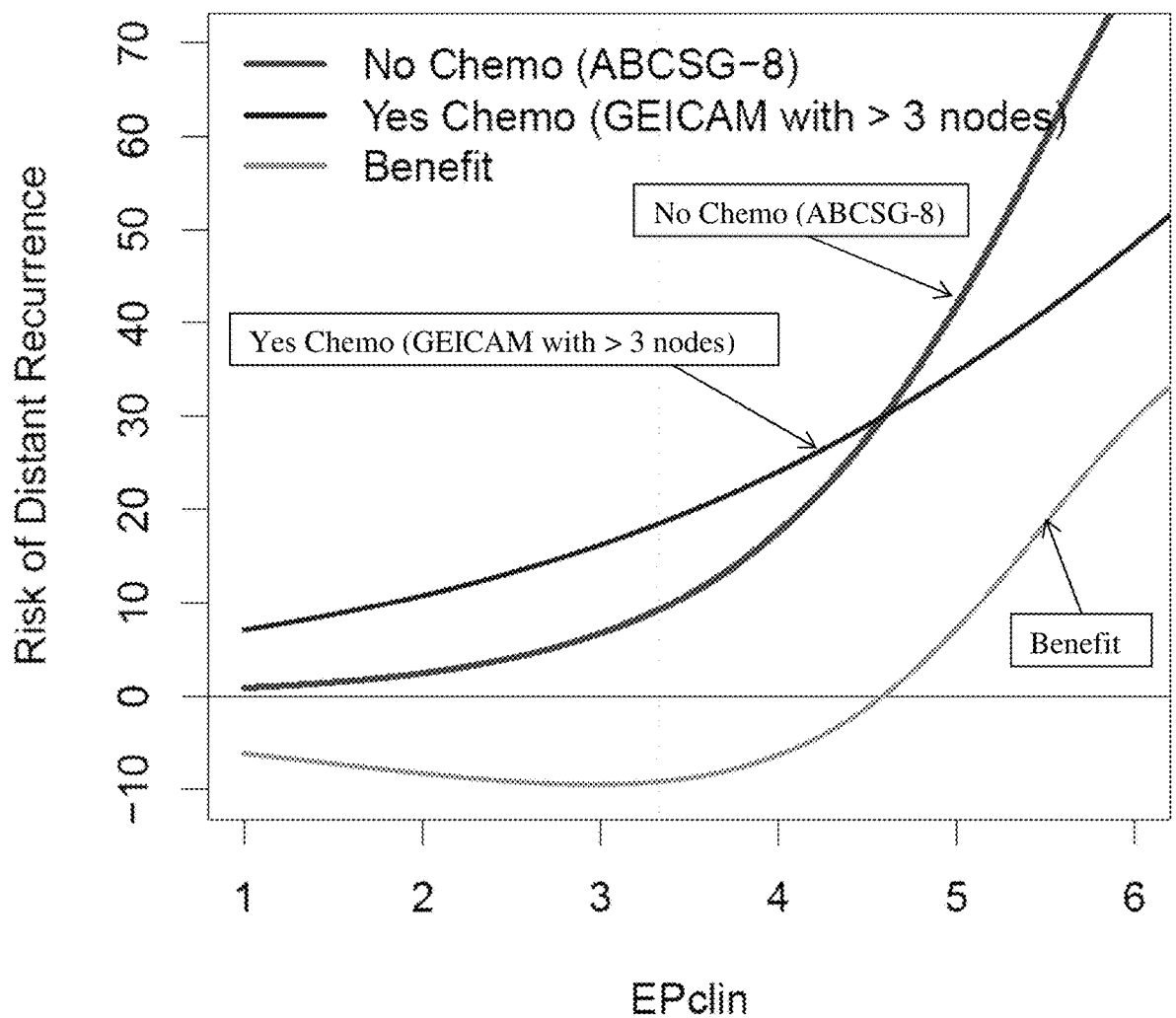
FIG. 3 demonstrates the use of EPclin to predict the benefit of chemotherapy in samples with >3 positive nodes.

The use of EPclin to predict the benefit of chemotherapy in node positive and node negative samples is illustrated in FIG. 1. The use of EPclin to predict the benefit of chemotherapy in samples with 1-3 positive nodes is illustrated in FIG. 2, and the use of EPclin to predict the benefit of chemotherapy in samples with >3 positive nodes is illustrated if FIG. 3.

CONCLUSION

The results suggest that EPclin scores can indicate the higher relative benefit of chemotherapy in node-positive/negative, and node-positive patients.

The invention claimed is:

1. A method for predicting a response to and/or a benefit of chemotherapy in a patient suffering from or at risk of developing recurrent neoplastic disease, the method comprising the steps of:
   (a) determining RNA expression level values of four or more of the following 8 genes in a tumor sample from the patient: UBE2C, BIRC5, DHCR7, STC2, AZGP1, RBBP8, IL6ST and MGP; or determining the RNA expression levels of four or more of the following 8 genes in a tumor sample from the patient: UBE2C, RACGAP1, DHCR7, STC2, AZGP1, RBBP8, IL6ST and MGP;
   (b) generating an expression score by combining the expression level values for the genes of the mentioned set recited in (a);
   (c) generating a clinical values score; and
   (d) combining the expression score with the clinical values score to generate a combined score, wherein the combined score is indicative of a prognosis for the patient.

2. The method of claim 1, wherein the neoplastic disease is a cancer.

3. The method of claim 2, wherein the cancer is breast cancer.

4. The method of claim 3, wherein the breast cancer is an estrogen receptor-positive and HER2-negative breast cancer.

5. The method of claim 2, wherein the chemotherapy is a neoadjuvant therapy.

6. The method of claim 2, wherein the prognosis is correlated to one or more distant metastases.

7. The method of claim 2, wherein the chemotherapy is adjuvant chemotherapy.

8. The method of claim 2, wherein the chemotherapy includes an anthracyclin-based therapy.

9. The method of claim 2, wherein the chemotherapy is 5-fluorouracil, epirubicin, and cyclophosphamide (FEC).

10. The method of claim 1, wherein the RNA expression levels have at least in part not been normalized before the mathematical combination.

11. The method of claim 2, wherein the clinical values score is generating by processing information regarding nodal status of the patient, the tumor size, or a combination thereof.

12. The method of claim 11, wherein the patient is node positive.

13. The method of claim 1, wherein the expression level is determined by at least one of a PCR-based method, a microarray-based method, a hybridization-based method, or a sequencing and/or next generation sequencing approach.

14. The method of claim 1, wherein the determination of expression levels is in a formalin-fixed paraffin-embedded tumor sample or in a fresh-frozen tumor sample.

15. The method of claim 1, wherein the expression level of the at least one marker gene is determined as a pattern of expression relative to at least one reference gene or to a computed average expression value.

16. The method of claim 1, wherein combining the expression score with the clinical values score comprises applying an algorithm to values representative of an expression level of a given gene, wherein the algorithm is a linear combination of the values representative of an expression level of a given gene or wherein a value for a representative of an expression level of a given gene is multiplied with a coefficient.

17. The method of claim 1, wherein one or more thresholds are determined for the combined score and wherein the thresholds are discriminated into high and low risk, high, intermediate and low risk, or more risk groups by comparing the combined score to the determined one or more thresholds.

18. The method of claim 1, wherein a high combined score indicates a benefit from a more aggressive therapy.

19. The method of claim 1, wherein the four or more genes comprises UBE2C, BRC5, DHCR7, STC2, AZGP1, RBBP8, IL6ST and MGP.

20. The method of claim 1, wherein the four or more genes comprises UBE2C, RACGAP1, DHCR7, STC2, AZGP1, RBBP8, IL6ST and MGP.

* * * * *